US009089576B2

(12) United States Patent
Piccirilli et al.

(10) Patent No.: US 9,089,576 B2
(45) Date of Patent: *Jul. 28, 2015

(54) MEDICAMENT COMPRISING A PEPTIDE EXTRACT OF AVOCADO, WHICH IS INTENDED FOR THE TREATMENT AND PREVENTION OF ILLNESSES THAT ARE LINKED TO AN IMMUNE SYSTEM DEFICIENCY OR OXIDATIVE STRESS OR SKIN AGEING OR DRY SKIN

(75) Inventors: Antoine Piccirilli, Villennes sur Seine (FR); Nathalie Piccardi, Arceau (FR); Philippe Msika, Versailles (FR); François Paul, Montgauch (FR); Stéphanie Bredif, Chaudon (FR)

(73) Assignee: LABORATOIRES EXPANSCIENCE, Courbevoie (FR)

( * ) Notice: Subject to any disclaimer, the term of this patent is extended or adjusted under 35 U.S.C. 154(b) by 1000 days.

This patent is subject to a terminal disclaimer.

(21) Appl. No.: 12/539,970

(22) Filed: Aug. 12, 2009

(65) Prior Publication Data

US 2010/0035816 A1    Feb. 11, 2010

Related U.S. Application Data

(63) Continuation-in-part of application No. 11/587,960, filed as application No. PCT/FR2005/001076 on Apr. 29, 2005, now Pat. No. 7,833,554.

(30) Foreign Application Priority Data

Apr. 30, 2004  (FR) .................................... 04 04640

(51) Int. Cl.
*A61K 36/00*   (2006.01)
*A61K 36/54*   (2006.01)
*A61K 31/198*  (2006.01)

(52) U.S. Cl.
CPC .............. *A61K 36/54* (2013.01); *A61K 31/198* (2013.01)

(58) Field of Classification Search
CPC ............................... A61K 36/00; A61K 36/33
USPC .................................................. 424/767, 775
See application file for complete search history.

(56) References Cited

U.S. PATENT DOCUMENTS

| 5,514,709 A * | 5/1996 | Counts et al. ............... 514/461 |
| 5,759,555 A * | 6/1998 | Moy ........................... 424/401 |
| 5,928,659 A   | 7/1999 | Moy |
| 6,146,616 A   | 11/2000 | Msika et al. |
| 6,348,271 B1  | 2/2002 | Nakata et al. |
| 6,582,688 B1  | 6/2003 | Broutin et al. |
| 6,861,077 B1  | 3/2005 | Cannell et al. |

| 2004/0013753 A1 | 1/2004 | Boumediene et al. |
| 2004/0018257 A1 | 1/2004 | Boumediene et al. |
| 2004/0022882 A1 | 2/2004 | Piccirilli et al. |

FOREIGN PATENT DOCUMENTS

| DE | 19852508 A1 | 5/2000 |
| FR | 2787714 A1 | 6/2000 |
| FR | 2 822 821 A1 | 10/2002 |
| FR | 2843027 A1 | 2/2004 |
| FR | 2 857 596 A1 | 1/2005 |
| JP | 02135260 A | 5/1990 |
| JP | 2004307456 A * | 11/2004 |
| WO | WO 98/47479 A1 | 10/1998 |
| WO | WO 99/43298 A1 | 9/1999 |
| WO | WO 01/21150 A1 | 3/2001 |
| WO | WO 01/21605 A2 | 3/2001 |
| WO | WO 01/68040 A2 | 9/2001 |
| WO | WO 2004/012496 A2 | 2/2004 |
| WO | WO 2004/012752 A2 | 2/2004 |
| WO | WO 2004/016106 A1 | 2/2004 |
| WO | WO 2004/050052 A1 | 6/2004 |
| WO | WO 2004/050079 A1 | 6/2004 |
| WO | WO 2004/112741 A1 | 12/2004 |
| WO | WO 2004/112742 A2 | 12/2004 |
| WO | WO 2005/102259 A1 | 11/2005 |
| WO | WO 2005/115421 A1 | 12/2005 |
| WO | WO 2007/057439 A1 | 5/2007 |
| WO | WO 2008/080974 A1 | 7/2008 |

OTHER PUBLICATIONS

Gowda et al. Structural Investigations on the mucilaginous polysaccharides Isolated from Bark of the Avocado Tree (*Persea americana* Mill)., Carbohydrate Research, 177, (1988), pp. 117-125.*
Kashman et al., "New Compounds from Avocado Pear," Tetrahedron, 1969, 25, 4617-4631.
Liu et al., "Human beta-defensin-2 production in keratinocytes is regulated by interleukin-1, bacteria, and the state of differentiation," Pub Med abstract, 2 pgs. (abstract as published in J. Invest. Dermatol., Feb. 2002, 118(2), 275-281).
Dvash et al., "Determination by Near-Infrared spectroscopy of Perseitol used as a Marker for the Botanical Origin of Avocado," *Journal of Agricultural and Food Chemistry*, vol. 50, pp. 5283-5287 (2002).
Perales et al., "Analysis of avocado allergen (Prs a 1) IgE-binding peptides generated by simulated gastric fluid digestion," *Journal of Allergy Clinical Immunology*, vol. 112, No. 5, p. 12 (2003).
Office Action issued on Oct. 27, 2009, by the Examiner in U.S. Appl. No. 11/587,960.
Office Action issued on Jun. 19, 2009, by the Examiner in U.S. Appl. No. 11/587,960.

* cited by examiner

Primary Examiner — Chris R Tate
Assistant Examiner — Deborah Davis
(74) *Attorney, Agent, or Firm* — Foley & Lardner LLP

(57) ABSTRACT

The invention relates to a medicament which comprises a peptide extract of avocado and which can also comprise a composition containing D-mannoheptulose an/or perseitol, such as a water-soluble extract of avocado sugars, and/or a peptide extract of lupine. The inventive medicament is intended for the treatment and/or prevention of illnesses that are linked to an alteration in innate and/or acquired immunity, through an increase in the production of anti-microbial peptides, preferably hBD-2, without inducing inflammatory reactions, irritations or intolerances.

13 Claims, No Drawings

MEDICAMENT COMPRISING A PEPTIDE EXTRACT OF AVOCADO, WHICH IS INTENDED FOR THE TREATMENT AND PREVENTION OF ILLNESSES THAT ARE LINKED TO AN IMMUNE SYSTEM DEFICIENCY OR OXIDATIVE STRESS OR SKIN AGEING OR DRY SKIN

This invention relates to a drug comprising an avocado peptide extract, advantageously for the treatment and/or prevention of diseases which are linked to an immunodeficiency, and more particularly to a deterioration of natural immunity or to oxidative stress.

The invention further relates a drug comprising an avocado peptide extract for aged or photo-aged skin or for dry and dehydrated skin.

All animals species daily confront a number of microorganisms, such as bacteria, fungi, parasites or viruses, which may affect their health or even their survival. Two defence systems oppose these micro-organisms: one which is called natural immunity, and is common to all animals, including man, and another immune system, called adaptative or specific, which is acquired through cells and mediators of immunity after contact with the potential attacker.

A difference between natural or adaptative immune responses may be found in the identification mechanisms for said micro-organisms. With natural immunity, the specificity of receptors is genetically determined since birth and is invariable. These receptors are expressed in cells such as some epithelium and endothelium cells, dendrite cells, monocytes and macrophages. All structures which are identified by natural immunity receptors are common to very many micro-organisms. Contrary to the adaptative immune response, the natural immune response mechanisms (phagocytosis, antimicrobial peptides, etc.) are activated as early as the beginning of an infection, and they control almost immediately the proliferation of pathogens which invade the host. The adaptative immune response then takes over.

Antimicrobial peptides have been found both in the vegetable and animal kingdoms, and over 500 different antimicrobial peptides have been discovered, from insects to man. Antimicrobial peptides are small molecules (10-50 amino acids), and are able to destroy a great variety of microorganisms (Gram+ or Gram− bacteria, fungi, viruses, transformed cells), by permeabilising their cell membranes. Moreover some of these antimicrobial peptides are able through chemo-attractive properties to recruit cells which participate in adaptive immunity such as dendrite cells or T lymphocytes. Many antimicrobial peptides have been detected in the vernix caseosa and in the amniotic fluid, as well as in newborn infants' skins, which suggests a key role in antimicrobial defence at the time of delivery, but also in the beginnings of life at a time when acquired immunity is still immature.

Most organisms synthesise several types of antimicrobial peptides in their various epithelia, in order to define a wide spectrum of activity. In mammals two main classes of antimicrobial peptides, whose production is induced during contact with a microorganism have been described: cathelicidins and defensins.

Human cathelicidin (LL-37) has been isolated for the first time from bone marrow cells. LL-37 is notably expressed in the human skin, in the region of the nails, as well as in that of the healthy and inflamed synovial membrane, especially with arthrosis patients. LL-37 has a wide spectrum of activity and seems to act synergistically with other antimicrobial peptides, notably defensins. LL-37 also has chemo-attracting properties, which makes it able to recruit adaptive immune cells.

Defensins are themselves divided into two families, or α and β, based on their secondary structure. α-defensins (6 are known to date) are mainly situated in the storage granules of specialized cells, such as neutrophils, or intestine Paneth cells, whereas β-defensins are a characteristic feature of epithelial tissues. Apart from their role in natural immunity, defensins are also known for their mitogenic properties, which suggest they might play a part in the healing processes.

In man, 4 β-defensins have been identified to date (over 20 genes coding for antimicrobial peptides seem to exist in our genome). Human β-defensin1 (hBD-1) is generally produced in a constitutive manner, and is abundantly expressed in the kidney, and, to a lesser extent, in the pancreas, salivary glands, airway epithelia, in woman's urogenital system, in the healthy synovial membrane, as well as in the placenta. hBD-1 is also expressed in the skin. Other forms of β-defensins, hBD-2, 3 and 4, are inductible. hBD-3 is also induced in the inflamed synovial membranes, such as for instance in arthrotic diseases. The expression of hBD-2 has to date been documented in the skin, the urogenital tract, the sweat glands, and the pilosebaceous unit.

In the skin other peptides or proteins, such as adrenomedullin, cystatin, the specific inhibitor of elastase/SKALP/elafin, would seem to possess antimicrobial activities. More recently dermicidine (with a wide spectrum of activity) has been characterised as an antimicrobial peptide which is specific to the skin, which would seem to be produced in the eccrine sweat glands, and whose secretion, together with sweat, would seem to make up an important part of the natural defence system against local and systemic infections. hBD-2 has been characterised for the first time in psoriasis scales. The expression of hBD-2, as well as of LL-37, is increased in psoriasis lesions, which would explain the greater resistance to infection of patients with this pathology. Conversely in atopic dermatitis (chronic lesions and budding lesions), the expression of LL-37 and hBD-2 decreases under the influence of interleukin-4 (IL-4) and interleukin-13 (IL-13), which are mediators of atopy. This insufficiency could explain the increased sensitivity to infection of patients with atopic dermatitis. In acne the expression of β-defensins (hBD-1 and 2) is increased as a reaction to the proliferation of *P acnes*. Moreover it is supposed that acneic patients would suffer from an initial imbalance in antimicrobial peptides, which would be responsible for bacterial proliferation. In their turn these bacteria would stimulate natural immune defences.

Inflammation thus seems to be a primary factor in the induction of antimicrobial peptides. Thus it also has been shown that interleukin-1, TNF-α (Tumour Necrosis Factor alpha) and ultraviolet irradiation would stimulate the production of hBD-2. The expression of hDB-2 is also linked to the differentiation stage of keratinocytes. Thus stimulating the production of antimicrobial peptides, notably within the defensin family, and more particularly of hBD-2, would make it possible to enhance and/or to restore natural immunity, especially in the eye and the epithelia (epidermis, vaginal, intestinal, nasal and auricular mucosae, and airways).

The buccal cavity is constantly open to a great variety of microorganisms (bacteria, viruses, fungi). Among other facts, it is well established that bacteria such as *Actinobacillus actinomycetemcomitans, Porphyromonas gingivalis*, are key factors participating in the development of peridontal diseases (gingivitis and parodontitis). The gingival epithelium is the first bastion against the various pathogens which may be found in the region of the mouth. As such gingival keratinocytes yield a wide panel of antimicrobial peptides, hBD-1, -2, -3, LL-37. These peptides are also produced in the buccal mucosa, as well as by salivary glands.

More particularly the stimulation of antimicrobial peptides would make it possible to enhance and/or to restore natural immunity in the healthy or diseased skin of newborn infants and children, whose immunity is generally deficient, and in the skin of adults or aged persons, whether in good health or not (immunodepressed). This stimulation would thus make it possible to advantageously supplement the skin's passive defence system as made up by the stratum corneum (corneocytes+intercellular cement), and to prepare the adaptive immune response in newborn infants, children, adults and aged persons, whether in good health or not. In the same manner, this stimulation would make it possible to accelerate healing.

The permeable barrier of the skin is located in the outer layer of the epidermis: the stratum corneum. Corneocytes (keratinocytes in an advanced differentiation state), the constituent cells of the stratum corneum, are coated in a lipid-enriched extracellular matrix. This lipid-rich matrix is the source of the permeable barrier function. The lipids in the stratum corneum essentially consist of ceramides (50% of the total lipid mass), cholesterol (25%) and free fatty acids (10%). The content of these three key lipids in the stratum corneum is reduced with age; this decrease would appear to be the result of a reduction in the activity of limiting enzymes in the synthesis pathways of these lipids.

Natural skin hydration is essentially due to its glycosaminoglycan content, and hyaluronic acid in particular. Glycosaminoglycans (GAGs) other than hyaluronic acid are molecules consisting of a peptide part and an oside part. They play a strong role in water retention in the dermis and this help maintain a satisfactory hydration level. Hyaluronic acid (HA) consists exclusively of oside molecules. It is particularly an important factor in epidermal thickening: with water, with which it binds strongly, it forms a dense viscoelastic network and thus takes part in skin density, cohesion, hydration and elasticity. With age, a decrease in the epidermal HA content occurs.

The dermis is a connective tissue consisting of various cell types, of which fibroblasts are the majority cells. However, cells are not the quantitatively majority constituents of connective tissues; a substantial part of the tissue volume is in fact occupied by a complex network referred to as the extracellular matrix (ECM).

The major role of dermal fibroblasts is the coordinated biosynthesis of ECM constituents, which are mainly responsible for the rheological properties of the skin and give it its mechanical resistance, suppleness and elasticity properties. The dermal ECM consists of a large number of different macromolecules which may be broken down into four families: the collagen and elastin families (fibrous macromolecules) and two glycoconjugate families: proteoglycans/glycosaminoglycans and structural glycoproteins.

Collagens represent approximately 70% of the constituents of the dermal ECM, with a majority of type I collagen (85-90% of dermal collagen) and type III collagen (10-15%). Firmness and resistance to pressure are essentially dependent on dermal fibrous collagens.

Elastic fibres are responsible for the skin's elasticity. They are the result of the assembly of two major constituents: elastin and fibrillin-rich microfibrils; elastin represents 1 to 3% of the dermis.

Skin modifications with age are the result of modifications of the cell functions and progressive modifications of the ECM composition and structure. In fact, the dermis is subject to a gradual loss of its thickness. General atrophy of the ECM occurs with a decline in the number of fibroblasts and a decrease in collagen and elastin along with poor collagen and elastic fibre organisation. This decrease in the quantity of collagen and elastin may be attributed to a decrease in their synthesis and/or an increase in their degradation.

While collagen fibres may be synthesised at all stages of life, elastic fibres are essentially synthesised during development and growth. Elastic fibre disorganisation is one of the major signs of skin ageing.

Unlike collagen fibres, elastic fibres are not assembled spontaneously, therefore, elastogenesis may be described in two essential stages:

a) tropo-elastin (soluble elastin precursor) deposition on a fibrillin-rich microfibil matrix;

b) cross-linking of tropo-elastin molecules by lysyl oxidases (LOX) resulting in the formation of an insoluble elastin polymer.

Lysyl oxidases catalyse covalent bond formation between the lysine residues of two adjacent tropo-elastin molecules by means of oxidative deamination. To date, five genes coding for five lysyl isoforms have been discovered: LOX, LOXL (Lysyl oxidase-like), LOXL2, LOXL3, LOXL4. Of these isoforms, only the mature enzymes, LOX and LOXL, have a proven role in elastogenesis. In addition to its role in elastogenesis during development, LOXL also has an important role in adult elastic fibre homeostasis. LOX is also involved in collagen fibre cross-linking. With age, LOX and LOXL expression decreases, resulting in poor tropo-elastin cross-linking which is therefore susceptible to enzyme degradations (matrix metalloproteinases, serine proteases, etc.). This elastic fibre loss due to enzyme degradation is an important factor in tissue ageing.

Matrix metalloproteinases (MMP) form a family of enzymes capable of degrading extracellular matrix compounds. 23 different MMPs have been identified in humans of which MMP1 (interstitial collagenase) is responsible for type I and III collagen degradation. MMP activity regulation may be carried out at different levels: in terms of genic transcription, in terms of pro-MMP activation or in terms of MMP inactivation by inhibitors. In the skin, MMPs are produced by different cell types including the fibroblast. They have a predominant role in skin ageing; in fact, age-related ECM loss results both from a decrease in matrix macromolecules synthesis and an MMP activation/inhibition imbalance. In this way, MMP1, MMP2, MMP3 and MMP9 are over-expressed in aged skin.

Mast cells are granular cells normally found in the dermis and which play an important role in allergic and inflammatory reactions. Tryptase is a serine protease stored in the secretory granules of mast cells, it represents 20% of the total proteins found in mast cell granules. During degranulation, the content of these granules, including tryptase, is released into the extracellular environment.

Chronic sun exposure has deep-rooted effects on the epidermis and dermis, resulting in the formation of wrinkles, sagging and slackness of the skin. UV irradiation and the normal ageing process may activate proMMPs resulting in the degradation of the dermal matrix. For a long time, this degradation by MMPs was considered to be the main mechanism involved in photo-ageing. However, the probable role of mast cell tryptase in photo-ageing was recently described. In this way, several studies have demonstrated a significant increase in the number of mast cells and the number of mast cells containing tryptase in UV-irradiated skin. Moreover, it was demonstrated that tryptase:

is capable of activating pro-MMP1 and that this activation results in the cleavage of collagen I (although the exact mechanism of action is not elucidated), is capable of activating pro-MMP9, appears to be capable of cleaving type IV and I collagens directly.

Thus, mast cell tryptase would appear to contribute to ECM degradation in two ways: by activating the latent forms of proteases degrading the ECM, and by direct degradation of the ECM constituents. One of the most important characteristics of mast cell-derived tryptase, compared to other skin proteases, is the absence of physiological inhibitors which therefore enables a prolonged enzyme action. In addition to its actions on extracellular matrix constituents, it has also been demonstrated that tryptase was capable of cleaving type IV collagen, one of the most important DEJ (Dermal-Epidermal Junction) proteins. In this way, an increase in mast cells in the inflammatory processes induced by chronic UV exposure could damage the DEJ. Moreover, tryptase could favour neutrophil infiltration significantly via PAR2 activation on the blood vessels during inflammatory processes. Neutrophil elastase has been described as one of the primary factors initiating photo-ageing. Thus, tryptase could favour the first stages of photo-ageing via different pathways.

Skin is constantly exposed to an array of chemical and physical environmental pollutants. These environmental toxicants or their metabolites are inherent oxidants and/or directly or indirectly drive the production of a variety of reactive oxidants also known as reactive oxygen species (ROS). ROS are short-lived entities that are continuously generated at low levels during the course of normal aerobic metabolism. ROS include singlet oxygen ($^1O_2$), superoxide anion ($O_2^-$), hydrogen peroxide ($H_2O_2$), the hydroxyl radical (OH), etc. The fundamental purpose of the release of large amount of ROS during the inflammatory process is to kill or destroy invading microorganisms and/or to degrade damaged tissue structures. It is the imprecise targeting of ROS that can induce oxidative stress in adjacent normal cells leading to enhancement of pathologic processes.

Cell ageing is accompanied by an accumulation of damaged proteins (by means of oxidation, glycation, conjugation with lipid peroxidation products). Under normal conditions, damaged proteins may be repaired by enzyme systems (such as the thioredoxin/thioredoxin reductase system or the peptide methionine sulphoxide reductase system) or eliminated by intracellular degradation via the proteasome.

Protein Oxidation:

ROS (Reactive Oxygen Species) formed in response to physiological or environmental processes (irradiations, inflammation, pollution . . . ) are capable of modifying proteins. In proteins, all amino acids may be oxidised, sulphurous amino acids (cysteine and methionine), and aromatic amino acids (tryptophan and tyrosine) being the most sensitive. Cysteine oxidation results in the formation of disulphide bridges, mixed disulphides and cysteic acids; these changes are reduced by enzyme repair systems such as thioredoxin and/or glutaredoxin. Methionine oxidation results in the formation of S and R methionine sulphoxide diastereoisomers which are reduced by peptides methionine sulphoxide reductases A (MsrA) and B (MsrB) respectively.

The oxidation of other amino acids generally results in the formation of hydroxyl and carbonyl derivatives. In addition, the detection of carbonyl groups associated with proteins is a method commonly used to evaluate the protein oxidation level.

Oxidised Protein Elimination or Repair Mechanisms:

The enzyme repair systems described above (thioredoxin/glutaredoxin/peptide methionine sulphoxide reductase) are the only oxidised protein repair mechanisms. However, in the event of irreversible protein modifications, such as carbonyl formation, the only way to eliminate these altered proteins is their selective degradation. There are two major proteolysis categories: the lysosomal (non-selective pathway) and the non-lysosomal or cytosolic pathway. The cytosolic pathway (involved in intracellular protein turnover and in abnormal and damaged elimination) is subdivided into two main proteolytic systems: calpaines (calcium-dependent neutral proteases), which are calcium-dependent and ATP-independent endoproteases; and the proteasome.

The proteasome is an intracellular molecular complex consisting of several subunits which enables degradation by means of proteolysis of different intracellular proteins including abnormal, incorrectly folded, denatured or otherwise damaged proteins along with perfectly normal proteins which need to be eliminated for the correct functioning of the cell. Therefore, the proteasome takes part in the elimination of damaged proteins and the continuous renewal of cell proteins. The proteasome is a high molecular weight protease (700 kDa) consisting of 28 subunits arranged in a barrel shape consisting of 4 heptameric rings of 18 to 35 kDa. The two outer rings each contain a copy of 7 different α type subunits. Similarly, each inner ring contains a copy of 7 different, but bound, β type subunits where the catalytic sites are located. The α subunits are devoided of proteolytic activity and are therefore assumed to be regulating subunits. On the other hand, β subunits contain catalytic peptidase activities:

the "peptidylglutamyl-peptide hydrolase" or PGPH activity is contained in subunit β1;

the "trypsin-like" activity is contained in subunit β2;

the "chymotrypsin-like" activity is contained in subunit β5.

Protein Oxidation and Age:

The "free radical" theory suggests that oxygenated free radicals are factors causing cell ageing giving rise to molecular damage, some of which would appear not be repaired and accumulate with age. In fact, in aged cells, damaged DNA, lipids and proteins accumulate, resulting in cell function impairment. Proteins may undergo various modifications (oxidation, glycation, conjugation with lipid peroxidation products), the incidence of which increases with age. The modifications impair their biological functions and are involved in age-related cell degeneration. In this way, cell ageing would appear to be dependant on three factors:

ROS production, anti-oxidant defences, the effectiveness of the systems responsible for damaged cell constituent elimination.

With age, an accumulation of oxidised proteins in the skin is observed, along with a decrease in the proteasome (in terms of activity and quantity). In this way, in a comparative study on fibroblasts in young cultures (low passages) and senescent cultures (high passages), a decrease in the activity of the three main enzyme activities of the proteasome associated with senescence was demonstrated. This decrease in activity is accompanied by a decrease in the levels of expression of subunits β1, β2 and β5 comprising the catalytic centres of these three enzyme activities. In parallel, an accumulation of oxidised proteins was observed in the senescent cells. The loss of proteosomal activity with age is therefore associated with incomplete oxidised protein degradation, an increase in protein aggregation and accelerated cell dysfunction.

In a surprising manner, the inventors have discovered that a composition comprising an avocado peptide extract makes it possible:

- to increase the production of antimicrobial peptides, advantageously of hBD-2;
- to stimulate dermal extracellular matrix metabolism;
- to protect the skin from ageing or photo-ageing by inhibiting tryptase release by mast cells;
- to protect the skin against oxidative stress; and
- to hydrate and relipidise skin.

Moreover, compositions comprising an avocado peptide extract have an hydrating and relipidising activity, provide protection against oxidative stress by improving elimination and repair of oxidised proteins activate the metabolism of the dermal extracellular matrix and have a protective activity against photo-ageing.

Thus the aim of the invention is a drug comprising an avocado peptide extract, which includes 2-10 weight % alpha-aminated nitrogen, in relation to the dry matter weight of the peptide extract, and a appropriate excipient.

In this invention, the phrase 'alpha-aminated nitrogen' means the nitrogen content of peptides in the form of free alpha-aminated groups. A measurement of the alpha-aminated nitrogen content of peptides allows one to evaluate the hydrolysis level of proteins as well as the average molecular weight of peptides.

The avocado peptide extract may be directly obtained from any part of the avocado or avocado tree, such as the fruit, the skin, the stone, the leaf or the roots of the tree. One may also obtain an avocado peptide extract from by-products of the avocado processing industry, of which may be cited, among others: the fresh avocado pulp, the quick frozen or dehydrated pulp, avocado cakes from oil extracting processes (mechanical and/or solvent extraction of the previously dehydrated fruit), de-oiled solid matter from wet oil extracting processes (so-called centrifugation process), de-oiled solid matter from enzymatic avocado oil extracting processes, raw mashed avocado (guacamole), solid refuse from plants manufacturing these mashed products. The extract is advantageously obtained from the fresh avocado tree fruit. Fruits may be chosen among the Hass, Fuerte, Ettinger, Bacon, Nabal, Anaheim, Lula, Reed, Zutano, Queen, Criola Serva, Mexicana Canta, Region Dschang, Hall, Booth, Peterson and Collison Red varieties, more advantageously the Hass, Fuerte and Red varieties. Preferably the Hass, Fuerte, Ettinger and Bacon varieties will be retained, and most preferably the Hass and Fuerte varieties.

The avocado tree fruit is principally made up of water, pulp, oil and a stone. The proportions of these various constituents are extremely variable, as is the case with all natural products. However one may generally assume the following average composition, as expressed in percentage of the fresh fruit, and shown in the following Table 1:

TABLE 1

| Water | 70-85% |
|---|---|
| Proteins | 1.5-4.5% |
| Lipids | 12-23% |
| Sugars | 1.5-5% |
| Fibres | 1.1-1.6% |

In relation to the pulp, the avocado proteins represent 1.5-2.5% (J. P. Gaillard, L'Avocatier, Edition G. P. Maisonneuve et Larose, 1987, pages 266-67). The distribution of amino acids, as expressed in weight percentage in relation to the total weight of amino acids, is shown in the following Table 2:

TABLE 2

| Alanine | 5-7 |
|---|---|
| Arginine | 3-5 |
| Aspartic acid | 8-12 |
| Cystine-Cysteine | <1 |
| Glutamic acid | 11-13 |
| Glycine | 4-6 |
| Histidine | 4-6 |
| Isoleucine | 4-7 |
| Leucine | 8-11 |
| Lysine | 4-7 |
| Methionine | 1-3 |
| Phenylalanine | 4-6 |
| Proline | 4-7 |
| Serine | 4-6 |
| Threonine | 4-6 |
| Tyrosine | 3-6 |
| Valine | 4-7 |

The main amino acids are glutamic acid, aspartic acid and leucine.

As compared with conventional oleoproteaceous plants such as soy bean, sunflower or rapeseed, the avocado is distinctly lower in protein content. Moreover, the fruit having a comparatively high fibre content, these proteins are made highly inaccessible through conventional chemical or biochemical paths. What is more, the natural macromolecules being hardly hydrosoluble, one tends to prepare hydrolysed fractions of these proteins (peptides), which are highly water-soluble and more easily bioavailable. Thus their allergenic power may also be eliminated. Therefore the invention also concerns the preparation of an avocado peptide extract via a gentle synthesis path which does not denaturate hydrolysed proteins.

More particularly the avocado peptide extract may be obtained by a process comprising the following steps:

- an avocado cake is obtained, advantageously from avocado fruit, through drying and extraction of the oil (lipids); after which
- said cake is ground in the cold (cryogrinding) and totally delipidated, then allowed to settle, centrifuged and collected; after which
- a first hydrolysis is carried out in the presence of glucanases, this being followed by a centrifugation process and the elimination of the soluble fraction;
- a second hydrolysis is carried out in the presence of one or more proteases, this being followed by a centrifugation process and the elimination of the residue; after which
- the peptide phase is concentrated by nanofiltration;
- a discoloration is carried out in the presence of activated carbon, for instance, this being followed by a simple filtration (10 μm), then by an ultrafiltration (cutting limit 10 kD); and finally
- if need be, a final sterilising microfiltration (0.2 μm), with preservative added and a packaging operation are carried out.

According to an advantageous variant of the invention, the first step of the process consists in drying, then deoiling the fruit. Thus after the fruit has been cut into thin slices it may be dried by any one of the set of techniques known to art specialists, among which may be cited hot air drying, freeze-drying or osmotic drying. Temperature during this drying step will generally be advantageously maintained below or at 80° C., whatever the technique which is used. Within this process, for reasons of easy implementation and cost, drying in ventilated dryers, in thin layer and under a hot air flow at a temperature between 70-75° C. is preferred. This operation may last between 5 and 72 hours.

Lipids in the dried fruit are later extracted either mechanically in a worm screw press, or chemically with a solvent such as hexane in a Soxhlet type extractor or in a De Smet type continuous band extractor, notably according to the process as described in French application FR 2 843 027, or by a process using supercritical $CO_2$. Among the main benefits of this process the oil by-product is a substance which may naturally be directly recycled. For this reason mechanical lipid extraction is preferred.

The dried and deoiled fruit, also called a cake, may then be subjected to the following steps:
- cryogrinding,
- total delipidation, notably with a non toxic food grade solvent such as ethanol and/or acetone,
- decanting and washing of the cake with water,
- centrifugation and collection of the cake,
- a first hydrolysis in the presence of one or several glucanases,
- centrifugation and discarding of the soluble fraction,
- a second hydrolysis in the presence of one or several proteases,
- centrifugation and discarding of the residue,
- concentration through nanofiltration,
- discoloration in the presence of activated carbon,
- a simple filtration (10 µm) followed by an ultrafiltration (cutting limit 10 kD),
- addition of a preservative, final sterilising microfiltration (0.2 µm) and packaging.

The final aqueous extract may contain 1-60 weight % dry matter, or 3-20% dry matter, preferably 5-6% dry matter. In relation to the dry matter weight, the mass content of alpha-aminated nitrogen may be between 2-10%, preferably between 5-7%. The pH value of a 1.2 weight % dry extract aqueous solution will generally be between 3-6, more advantageously between 4-5. Mean analytic data for a 1.2 weight % dry extract aqueous solution, as obtained by the above described process, are shown in the following Table 3:

TABLE 3

| | |
|---|---|
| Alpha-aminated nitrogen (called "o-phthalaldehyde" or "ninhydrine" method) (as a mass % in dry matter) | 4-10 |
| Proteins (as a mass % in dry matter) (N × 6.25)[1] | 10-30 |
| pH value (¼ dilution) | 4.5-7.0 |
| Absorbance (¼ dilution) 420 nm | 0.1-0.6 |
| Absorbance (¼ dilution) 550 nm | 0.02-0.1 |

[1] N × 6.25 corresponds to a total nitrogen (N) dosage of a sample, multiplied by a coefficient which is specific for the assayed protein. When the coefficient for assayed proteins is not known with precision, a coefficient of 6.25 is conventionally used.

The following Table 4 shows the average amino acid composition of the peptide extract as obtained by the inventive process, in which the values are expressed in weight % in relation to the total weight of assayed amino acids.

Values for aspartic acid and glutamic acid also include asparagine and glutamine contents, respectively.

TABLE 4

| Amino acid | Minimum value | Maximum value |
|---|---|---|
| Alanine | 6.4 | 7.8 |
| Arginine | 4.7 | 5.7 |
| Aspartic acid | 10.3 | 12.7 |
| Cystine-Cysteine | 2.9 | 3.5 |
| Glutamic acid | 13.0 | 15.8 |
| Glycine | 5.3 | 6.5 |

TABLE 4-continued

| Amino acid | Minimum value | Maximum value |
|---|---|---|
| Histidine | 2.2 | 2.6 |
| Isoleucine | 4.8 | 5.8 |
| Leucine | 7.6 | 9.4 |
| Lysine | 3.0 | 3.8 |
| Methionine | 1.2 | 1.6 |
| Phenylalanine | 4.7 | 5.7 |
| Proline | 4.1 | 5.2 |
| Serine | 5.5 | 6.7 |
| Threonine | 4.6 | 5.6 |
| Tyrosine | 3.6 | 4.4 |
| Valine | 5.8 | 7.2 |

Tryptophan not assayed.

The obtained extract may be freeze-dried in order to obtain a solid power (dry extract), but it is totally hydrosoluble in relation to the original avocado proteins.

According to an advantageous variant of the invention, at least 50% of the extract peptides are made up of 10-30 amino acid sequences. The size of these peptides is therefore much smaller as compared with that of the avocado's native proteins. Therefore these peptides thus possess a much better bioavailibility, notably on the skin.

The drug of the invention is particularly appropriate for the treatment and/or the prevention of diseases which are linked to a change in natural and/or acquired immunity, through an increase in the production of antimicrobial peptides, belonging to the cathelicidin and/or beta-defensin families, advantageously hBD-2. In the sense of this invention, a 'change' may mean an increase or a decrease.

The drug of the invention is also particularly appropriate for the treatment and/or prevention of diseases as linked to a change in natural and/or acquired immunity through stimulation of antimicrobial peptides like a specific elastase inhibitor, particularly elafin (SKALP).

The drug of the invention makes it possible to advantageously stimulate and/or supplement natural and/or acquired immunity.

In another embodiment, the drug of the invention is appropriate to improve the skin hydration and to improve the skin's action as protective barrier against environmental attacks and against water loss.

In another embodiment, the drug of the invention is appropriate to activate skin cell proliferation: epidermal keratinocytes and dermal fibroblasts.

In another embodiment, the drug of the invention is appropriate to improve skin's elasticity, skin's firmness and resistance to pressure.

In another embodiment, the drug of the invention is appropriate for inhibiting tryptase release by mast cells.

In another embodiment, the drug of the invention is appropriate to protect the skin against oxidative stress. In particular, the drug is able to decrease the formation of lipid peroxides induced by oxidative stress. Moreover, the drug is able to stimulate the expression of thioredoxin, an enzyme responsible for oxidised protein repair. In addition, by stimulating expression of proteasome β1 subunit in young and aged fibroblasts, the drug is able to facilitate the treatment (repair/elimination) of oxidised proteins, which are deleterious for epidermal and dermal homeostasis. Furthermore, the drug is able to limit the accumulation of oxidised proteins induced by fibroblast ageing.

Within the scope of the invention, said diseases may generally be linked to the presence of microorganisms, notably Gram+ and/or Gram− bacteria, fungi or viruses.

More particularly said diseases may be infections of the organs of sight and audition, non keratinized epithelia (vaginal, intestinal, gingival, nasal, pulmonary, respiratory tract, anal and urethral mucosae) and keratinized epithemia such as the skin. Said diseases may also be infections of the teguments or skin phanerae (hair, nails, sweat glands, sebaceous glands). Thus said diseases may be pathologies such as folliculitis, furuncles, abscess, impetigo or whitlow.

Said diseases may be pathologies of the scalp such as dandruffs and in a wider sense conditions linked to a hyperseborrhoea.

Said diseases may be pathologies which are linked to a change in the Th1/Th2 balance, such as atopic dermatitis.

Said diseases may be pathologies which are linked to changes in the synthesis of cytokins, such as IL-4 and/or IL-13, notably within the frame of atopic dermatitis.

Said diseases may also be inflammatory dermatoses, such as atopic dermatitis, atopic eczema and/or contact dermatitis, psoriasis, acne and itching dermatites.

Said diseases may also be burns, particularly first or second grade burns.

Said diseases may also be pathologies which are linked to a deficiency in the skin barrier. Thus the inventive drug may be used for the treatment of hyperreactive skins (sensitive, irritated, allergic), atopic, dry or aged skins. Said diseases may also be pathologies which are linked to skins made vulnerable by aggression from the environment, notably due to cold, pollution, stress, tobacco or sun exposure.

Within the scope of this invention, the drug is also appropriate for the protection of immature, healthy or pathological skins in newborn infants and children. Indeed it allows one to reinforce the natural defences of a child's epidermis when immunity is generally deficient.

Within the scope of this invention the drug is also appropriate for the protection of healthy or pathological skins in adults or in the elderly, notably with immunodepressed persons.

The inventive drug is also appropriate for enhancing the healing process, whether normal or pathological, such as ulcers or bedsores.

Within the scope of this invention the drug is also aimed for the treatment and/or prevention of periodontal diseases, inflammatory articular pathologies such as arthrosis, infections of the mucosae, notably the vaginal, intestinal, respiratory, nasal or auricular mucosae, or the infections of the sight organs.

Within the scope of this invention, the drug is also intended for the treatment of aged skin, inflammated skin, allergic skin, photo-aged skin, wrinkled skin, dry skin.

According to an advantageous variant of the invention the drug comprises 0.1-20 dry weight % avocado peptide extract, in relation to the total weight of said drug, more advantageously 0.1-15 dry weight % avocado peptide extract, more advantageously still 0.5-10 dry weight % avocado peptide extract, more advantageously still 0.7-8 dry weight % avocado peptide extract, and more advantageously still 1-5 dry weight % avocado peptide extract.

According to an advantageous variant of the invention the drug moreover comprises D-mannoheptulose and/or perseitol (C7 sugars) or one of their chemical derivatives, advantageously in an amount of 0.001-30 dry weight %, in relation to the total weight of the drug, more advantageously 0.01-20 dry weight %, more advantageously still 0.1-10 dry weight %, more advantageously still 0.5-5 dry weight %.

A synergistic effect is then advantageously observed.

The D-mannoheptulose and/or perseitol source is advantageously either a hydrosoluble sugar extract from avocado or other plants. Otherwise D-mannoheptulose and perseitol are commonly marketed (synthetic origin).

According to an advantageous variant of the invention the D-mannoheptulose and/or perseitol source is an avocado sugar hydrosoluble extract comprising at least 50 weight % C7 sugars, in relation to the total weight of the extract dry matter (WO 2005/115421).

The avocado sugars hydrosoluble extract may be obtained by a process which comprises the following sequence of steps:
  obtaining an avocado cake, advantageously from avocado fruit, by drying the avocado and extracting the lipids (oil); followed by
  cryogrinding and total delipidation of said cake, then settling and centrifugation in order to collect a soluble fraction having a high C7 sugars content (discarding of the cake);
  demineralisation on an ionic resin of said soluble fraction as obtained in the preceding step; followed by
  an ultrafiltration at 10,000 Daltons;
  if need be, concentration by vacuum vaporising, addition of a preservative, sterilisation by microfiltration (0.2 μm) and packaging.

According to a preferred variant of the invention, the processes whereby the avocado cake is obtained and the lipids are extracted are advantageously carried out in an identical manner for the avocado peptide extract and the avocado sugars.

The dried and deoiled fruit, also called cake, may then be subjected to the following steps:
  cryogrinding,
  total delipidation, advantageously with ethanol and/or acetone,
  settling and washing the cake with water,
  centrifugation and collection of the soluble fraction (discarding of the cake),
  demineralisation by passing over ion exchange resins,
  ultrafiltration with a cut-off limit of 10 kD,
  vacuum concentration, addition of a preservative and packaging.

The final aqueous extract may generally contain 0.1-10 weight % dry matter, advantageously 1-7 weight % dry matter, more advantageously 3-5% dry matter. The C7 sugar, that is D-mannoheptulose and perseitol content in the dry matter is advantageously above 50 weight %, more advantageously between 65-90 weight %, in relation to the total dry matter weight.

The relative sugar composition of the avocado hydrosoluble extract, as expressed in weight in relation to the total weight of the extract dry matter, advantageously fills the following criteria (relative composition as determined by HPLC):

| D-mannoheptulose | 5-80% |
| --- | --- |
| Perseitol | 5-80% |
| Sucrose | <10% |
| Glucose | <10% |
| Fructose | <10% |

The avocado sugar hydrosoluble extract advantageously comprises, in relation to the total dry matter weight, 1-99 weight % mannoheptulose, more advantageously 5-80 weight % mannoheptulose, more advantageously still 10-80 weight % mannoheptulose. The avocado sugar hydrosoluble extract advantageously comprises, in relation to the total dry matter weight, 20-80 weight % perseitol, more advantageously 25-70 weight % perseitol.

Preferably the relative sugar composition of the hydrosoluble extract, as expressed in weight in relation to the total extract dry matter weight, fills the following criteria (relative composition as determined by HPLC):

| | |
|---|---|
| D-mannoheptulose | 25-60% |
| Perseitol | 25-60% |
| Sucrose | <10% |
| Glucose | <10% |
| Fructose | <10% |

If need be the obtained extract may be freeze-dried in order to obtain a solid powder (dry extract) which is totally hydrosoluble.

According to an advantageous variant of the invention, the inventive drug moreover comprises a lupine peptide extract, advantageously in a mass amount, in relation to the total drug weight, between 0.001-30 dry weight %, more advantageously still between 0.01-10 dry weight %. The lupine peptide extract, as added into the inventive composition, comprises at least 70 weight % peptides, advantageously at least 80 weight %, in relation to the dry matter weight of the peptide extract. A synergistic effect is then advantageously observed.

Particularly the lupine peptide extract may be obtained by a process which comprises the following steps:
- preparation of a ground lupine cake or a micronised lupine flour cake;
- followed by delipidation through solvent extraction;
- extraction of soluble protein and osidic fractions, or precipitation of proteins at the isoelectric point;
- if need be, separation of the protein fraction;
- enzyme hydrolysis of the protein fraction, and collection, possibly after filtration, of the peptide extract.

A process for preparing a peptide extract is described in French patent publication FR 2 792 202, filed by Expanscience Laboratories.

The drug of the invention may moreover comprise at least one compound as chosen within the group made up by emollients, moisturising active substances notably the active substance cupuaru butter, activators of keratin synthesis, keratoregulators, keratolytics, restructuring agents for the skin barrier (skin lipid synthesis activators, PPARs or Peroxysome Proliferator Activated Receptors agonists), activators in the differentiation of keratinocytes (retinoids, Calcidone®, calcium), antibiotics, antibacterial agents, antifungic agents, antiviral agents, seboregulators, such as 5-alpha reductase inhibitors, notably the active substance 5-alpha Avocuta®, as marketed by Expanscience Laboratories, immunomodulators, such as tacrolimus, pimecrolimus, oxazolines, preservatives, anti-itching agents, soothing agents, filters and sunscreens, anti-oxidant agents, growth factors, healing agents or eutrophic molecules, anti-inflammatory drugs and agents, and compounds containing vegetable oil insaponifiables.

The keratin synthesis activators which may be used within the scope of this invention in association with the avocado peptide extract, are advantageously retinoids, lupine peptides (as marketed by Expanscience laboratories, WO2005/102259), avocado sugars (WO 2005/115421), quinoa peptides extract (WO2008/080974) key proteins of the stratum corneum or granulosum (keratins).

Antibiotics which may be used within the scope of this invention, in association with the avocado peptide extract, are advantageously fucidic acid, penicillin, tetracyclines, pristamycin, erythromycin, clindamycin, mupirocin, minocycline, and doxycycline. Antiviral agents which may be used within the scope of this invention, in association with the avocado peptide extract, are advantageously acyclovir and valacyclovir. Anti-itching agents which may be used within the scope of this invention, in association with the avocado peptide extract, are advantageously glycine, lupine sugars and/or peptides (WO2005/102259), Cycloceramide® (WO2004050052, WO2004050079, et WO2004112741).

Soothing and anti-irritating agents which may be used within the scope of this invention, in association with the avocado peptide extract, are advantageously alpha bisabolol, liquorice derivatives, cycloceramides®, lupine peptides, quinoa peptides extract, lupine sugars and/or peptides, arabinogalactane, avocado sugars. Keratoregulators which may be used within the scope of this invention, in association with avocado peptide extract, are advantageously alpha hydroxy acids and their derivatives. A keratolytic substance which may be used within the scope of this invention, in association with the avocado peptide extract, is notably salicylic acid and its derivatives. Anti-oxidant agents which may be used with the scope of this invention, in association with the avocado peptide extract, are advantageously vitamins (C, E), trace elements (copper, zinc, selenium). Growth factors which may be used within the scope of this invention, in association with the avocado peptide extract, are advantageously becaplermine and TGF beta (Trasforming Growth Factor beta).

Healing agents which may be used within the scope of this invention, in association with the avocado peptide extract, are advantageously vitamin A, panthenol, Avocadofurane® (WO 01/21605), quiona peptides extract (WO 2008/090974), maca peptides extract (WO2004/112742), lupeol (FR 2 822 821, FR 2 857 596), arabinogalactane, zinc oxide, magnesium, silicon, Centella asiatica extracts such as madecassic or asiatic acid.

Drugs which may be used within the scope of this invention, in association with the avocado peptide extract, are advantageously drugs which are appropriately delivered topically or orally, for the prevention and/or treatment of atopy (corticoids, emollients), acne (antibiotics, benzoyl peroxide, retinoids, azelaic acid, vitamin PP, zinc, cyclines), of eczema (immunomodulators, emollients, salmon oil, borage oil, prebiotics) or of psoriasis (corticoids, calcipotriol, calcitriol, tazarotene, cade oil, acitretin, PUVA therapy).

Anti-inflammatory agents which may be used within the scope of this invention, in association with the avocado peptide extract, are advantageously steroidal anti-inflammatory agents (AIS), such as corticoids, or non steroidal agents (AINS). Restructuring agents of the skin barrier, which make it possible to stimulate the synthesis of key lipids in the epidermis, and which may be used within the scope of this invention, in association—advantageously with a synergistic effect—with the avocado peptide extract, are advantageously sunflower concentrates, more advantageously linoleic sunflower concentrates, such as the active substance as marketed by Expanscience Laboratories, Sunflower seed oil unsaponifiables or Soline® (see International Application WO 01/21150), vegetable oil insaponifiables, such as Avocadofurane® (see International Application WO 01/21150), PPARs agonists (rosiglitazone, pioglitazine). Restructuring agents are advantageously present in proportions between 0.001 and 30 weight %, in relation to the total weight of the drug. Antifungal compounds which may be used within the scope of this invention, in association with the avocado peptide extract, are advantageously econazole and ketoconazole.

Antiseptic preservatives which may be used within the scope of this invention, in association with the avocado peptide extract, are for instance triclosan, chlorhexidine, quaternary ammonia.

Immunomodulators which may be used within the scope of this invention, in association with the avocado peptide extract, are advantageously tacrolimus, pimecrolimus, oxazolines and oxazolidinones.

Oxazolines which may be used within the scope of this invention, in association—advantageously with a synergistic effect—with the avocado peptide extract, are advantageously oxazolines which are chosen among the group made up by 2-undecyl-4-hydroxymethyl-4-methyl-1,3-oxazoline, 2-undecyl-4,4-dimethyl-1,3-oxazoline, (E)-4,4-dimethyl-2-heptadec-8-enyl-1,3-oxazoline, 4-hydroxymethyl-4-methyl-2-heptadecyl-1,3-oxazoline, (E)-4-hydroxymethyl-4-methyl-2-heptadec-8-enyl-1,3-oxazoline, 2-undecyl-4-ethyl-4-hydroxymethyl-1,3-oxazoline. In a still more advantageous manner, said oxazoline is 2-undecyl-4,4-dimethyl-1,3-oxazoline, called OX-100 or Cycloceramide® (WO 2004/050079, WO 2004/112741).

Oxazolidinones which may be used within the scope of this invention, in association—advantageously with a synergistic effect—with the avocado peptide extract, are advantageously oxazolidinones disclosed in the international application WO 2004/050052.

The compounds which contain vegetable oil unsaponifiables, and which may be used within the scope of this invention, in association, advantageously with a synergistic effect, with the avocado peptide extract, are preferably chosen within the group made up by avocado furane lipids, avocado and soy bean unsaponifiables, lupine oil concentrates, sunflower oil concentrates, and their mixtures.

The avocado furane lipids which may be used within the scope of this invention, in association, advantageously with a synergistic effect, with the avocado peptide extract, are preferably natural 2-alkyl furanes, notably the active substance Avocadofurane® as marketed by Expanscience Laboratories, which may be obtained by the process as described in International Application WO 01/21605.

Avocado and soy bean unsaponifiables which may be used within the framework of this invention, in association, advantageously with a synergistic effect, with the avocado peptide extract, are preferably a mixture of furane avocado unsaponifiables and soy bean unsaponifiables, in a respective ratio of about 1/3-2/3. Avocado and soy bean insaponifiables are more advantageously the product Piascledine®, as marketed by Expanscience Laboratories.

Lupine oil concentrates which may be used within the scope of this invention, in association, advantageously with a synergistic effect, with the avocado peptide extract, are advantageously concentrates which are obtained through molecular distillation of lupine oil, advantageously sweet white lupine oil, such as those described in International Application WO 98/47479. They contain, advantageously, some 60 weight % unsaponifiables.

The sunflower oil concentrates which may be used within the scope of this invention, in association, advantageously with a synergistic effect, with the avocado peptide extract, are advantageously linoleic sunflower concentrates, such as the active substance marketed by Expanscience Laboratories, Soline® (see International Application WO 01/21150).

Can also be used in association within the scope of the invention the following compounds: Lupeol (as described in patents FR 2 822 821 and FR 2 857 596), lipoic acid, enoxolone, ectoine, caffeine, manganese, hyaluronic acid, pyrrolidone carboxylic acid and derivatives thereof, ceramides, cholesterol, squalane, phospholipids, beta carotene, vitamin B3 (niacinamide, nicotinamide), vitamin B6, urea, coenzyme Q10, glucosamine and salts thereof, N acetyl glucosamine, thermal or spring water (Avene, La Roche Posay, Saint Gervais, Uriage, Gamarde), soy bean peptides, arabinogalactane (in particular an association of arabinogalactane and lupeol or soy peptides), avocado oil (WO2004/012496, WO2004/012752, WO2004/016106, WO2007/057439), genistein, canola seed concentrate, or corn concentrate.

Furthermore, the avocado peptidic extract, alone or used in association with anyone of the above cited active agents, is advantageously combined with solar protective agents, such as UVA and/or UVB sunfilter or UVA and/or UVB sunscreens, mineral or organic sunscreens or filters known by the skilled person. The choice of appropriate solar protective agent and its concentration is easily done by the skilled person for any seek protection degree.

Particular solar protective agents can be: titane oxide, zinc oxide, Methylene bis-benzotriazolyl tetramethylbutylphenol and Bis-ethylhexyloxyphenol methoxyphenyl triazine.

The drug of the invention is aimed at the treatment and/or prevention of diseases which may affect man and/or animals, notably mammals. The drug of the invention may be formulated in the form of various preparations which are adapted for topical administration, for oral, rectal, vaginal, nasal, auricular or bronchial administration, for parenteral administration. Preferably the various preparations are adapted for topical administration and include creams, ointments, lotions, oils, patches, sprays, or any other product for external application. Routes for administrating the inventive compounds and compositions, optimal dosage and drug forms may be determined following criteria which are generally taken into account in establishing a pharmaceutical treatment, particularly in the fields of dermatology or veterinary medicine, as adapted to a patient or an animal, such as, for instance, the age or body weight of the patient or animal, the seriousness of his/its condition, tolerance towards the particular treatment, the side effects observed, and the type of skin. According to the type of administration which is sought, the inventive drug and/or active substances may moreover comprise at least one pharmaceutically suitable, notably dermatologically suitable, excipient. One may preferably use an excipient which is adapted for topical external administration. The inventive drug may moreover comprise at least one pharmaceutically known additive, as pharmaceutically known to art specialists, chosen among thickeners, preservatives, perfumes, colouring agents, chemical filters or minerals, moisturising agents, thermal waters, etc.

This invention also relates to a cosmetic composition comprising an avocado peptide extract and a cosmetically suitable appropriate excipient. The avocado peptide extract advantageously comprises 2-10 weight % alpha-aminated nitrogen, in relation to the dry matter weight of the peptide extract.

The cosmetic composition of the invention advantageously comprises 0.001-30 dry weight % avocado peptide extract, in relation to the total weight of said composition, more advantageously still 0.01-10 dry weight % avocado peptide extract. According to a preferred version of the invention the avocado peptide extract may be obtained according to a process such as previously described.

According to an advantageous version of the invention, the composition moreover comprises D-mannoheptulose and/or perseitol (synergistic effect), advantageously in an amount of 0.001-30 dry weight %, more advantageously still 0.01-5 dry weight %, in relation to the total weight of the composition. The D-mannoheptulose and/or perseitol source is advantageously a hydrosoluble avocado sugars extract, whose C7 sugar content—that is to say the D-mannoheptulose and perseitol content—in the dry matter is advantageously between 65-90 weight % in relation to the total dry matter weight.

These heptitol type sugars may also be obtained from another vegetable source or by synthesis.

According to an advantageous variant of the invention, the composition moreover comprises a lupine peptide extract (synergistic effect), advantageously in an amount of 0.001-30 weight %, in relation to the total weight of the composition. The lupine peptide extract, as added into the inventive composition, comprises at least 70 weight %, advantageously at least 80% peptides, in relation to the dry matter weight of the peptide extract. It may be obtained according to a process such as here above described.

The composition may moreover contain at least one compound chose among the group made up by the skin barrier's restructuring agents and compounds containing vegetable oil unsaponifiables, such as here above defined. In particular the cosmetic composition may contain an active substance chose among the group made up by Soline®, Avocadofurane® and Piasclédine®, as marketed by Expanscience Laboratories.

The cosmetic composition of the invention comprises advantageously 0.001-30 weight %, in relation to the total weight of the composition, of at least one skin barrier restructuring agent.

The cosmetic composition of the invention may be formulated in the form of various preparations adapted for topical administration, oral, rectal or vaginal administration, or parenteral administration. Preferably the various preparations are adapted for topical administration and include creams, ointments, lotions, oils, patches, sprays or any other products for external application. According to the type of administration which is aimed at, the inventive composition and/or active compounds may moreover comprise at least one cosmetically suitable excipient. The inventive cosmetic composition may moreover comprise at least one additive which is known to the art specialist, and chosen among thickeners, preservatives, perfumes, colouring agents, chemical fibres or minerals, moisturising agents, thermal waters, etc.

This invention also relates to a method for the cosmetic treatment of sensitive, irritated, intolerant skins and/or mucosae, skins and/or mucosae which present cutaneous reddenings, or a non pathological immunological imbalance, characterised in that it implies applying onto the skin and/or the mucosae a cosmetic composition of the invention.

This invention also relates to a method for the cosmetic treatment of aged, inflammed, allergic, photo-aged, wrinkled, dry skins and/or mucosae, wherein it implies applying onto the skin and/or mucosae the cosmetic composition of the invention.

This invention finally relates to a neutraceutic composition comprising an avocado peptide extract, and, if need be, a suitable appropriate excipient. The avocado peptide extract advantageously comprises 2-10 weight % alpha-aminated nitrogen, in relation to the dry matter weight of the peptide extract.

The neutraceutic composition of the invention advantageously comprises 0.001-30 weight % avocado peptide extract, in relation to the total weight of said composition, more advantageously 0.01-10 weight % avocado peptide extract. According to an advantageous variant of the invention, the avocado peptide extract may be obtained according to a process such as here above described.

According to an advantageous variant of the invention, the neutraceutic composition also comprises D-mannoheptulose and/or perseitol (synergistic effect), advantageously in an amount of 0.001-30 dry weight %, in relation to the total weight of the composition. The D-mannoheptulose and/or perseitol source is advantageously an avocado sugar hydrosoluble extract, whose C7 sugar content, that is to say the D-mannoheptulose and perseitol content in the dry matter is advantageously between 65-90 weight %, in relation to the total dry matter weight.

According to an advantageous variant of the invention, the neutraceutic composition comprises at least a lupine peptide extract (synergistic effect), advantageously in an amount of 0.001-30 dry weight %, in relation to the total weight of the composition. The lupine peptide extract, as added into the inventive composition, comprises at least 70 weight %, advantageously at least 80% peptides, in relation to the peptide extract dry matter weight. It may be obtained according to a process such as here above described.

The following non limitative Examples illustrate the invention.

EXAMPLE 1

Preparation of an Avocado Peptide Extract 50 kg fresh avocado, Hass variety, are cut into thin slices, 2-5 mm thick, stone included, with a disk cutting machine. The drying apparatus is a hot air flow thermoregulated oven. Once cut the avocados are distributed into 4-5 cm thick layers onto trays which are laid out in tiers. Drying temperature is set at 80° C. for a total duration of 48 hours. One dried the fruits are exposed to cold pressure. This operation is carried out on a small Komet® laboratory press.

The 4 kg delipidated pieces of fruit (cake) are then broke at a cold temperature, then extracted with reflux, in the presence of 25 liters of ethanol. The powder, with the lipids exhausted, is then collected by filtration onto a Büchner funnel, and dried in the oven at 50° C. during 5 hours.

The cake is then washed with demineralised water (10 l), then separated by centrifugation. The solid fraction is taken up in an aqueous solution, acidified with HCl (with a pH value set at 5), then brought in the presence of 2% cellulase (in relation to dry matter) Duration of the hydrolysis is set at 6 hours.

The mixture is then centrifuged at 2,000 g in the presence of an additive (2.5% p/v). The residue which is collected is then subjected to a second hydrolysis at a pH value of 8.0, in the presence of 0.5% protease, at a temperature of 55° C., during 2 hours. Hydrolysis is regulated at a constant pH value by the continuous addition of 2 M sodium hydroxide. The protease is finally denaturated by heating during 10 minutes at 85° C.

The mixture as obtained is centrifuged and the supernatant is filtrated by passing through a 7.5 μm membrane. It is then ultrafiltrated on membranes having a 10 kD cut-off limit.

The raw peptide extract as obtained with 20% dry matter is discoloured in the presence of 1% activated carbon, then again filtrated through a 7.5 μm membrane. The discoloured extract is then microfiltrated (0.2 μm), its supplemented with a preservative and finally packaged after a sterilising filtration (0.2 μm).

Characteristic data of the hydrosoluble avocado peptide extract (5% dry matter) as obtained by this process are shown in the following Table 5:

TABLE 5

| Appearance | Slightly orange-coloured solution |
|---|---|
| Analytic criteria | |
| Dry matter | 5% |
| pH value (¼ dilution) | 4.5 |

TABLE 5-continued

| | |
|---|---|
| Absorbance at 420 nm (¼ dilution) | 0.152 |
| Absorbance at 550 nm (¼ dilution) | 0.035 |
| Dry matter composition | |
| Alpha-aminated nitrogen | 6.7% |
| Proteins | Not detected |
| Preservative | 0.4% |

In the following Table 6, the molecular mass distribution in the avocado peptide extract as obtained by this process is given:

TABLE 6

| HPLC peak | Molecular mass (g/mol) | Average number of amino acids | Relative % |
|---|---|---|---|
| 1 | >3480 (1) | <29 | 1% |
| 2 | 3480-1180 | 29-9 | 26% |
| 3 | 1180-310 | 9-2 | 45% |
| 4 | 310-130 | 2-1 | 15% |
| 5 | <130 | 1 | 13% |

(1) mass < 10000 g/mol

It may be observed that at least 27% of peptides in the extract are made up at least 9 amino acid sequences. Therefore the size of peptides in the extract is very small in relation to that of the natural proteins in the avocado. Thus these peptides possess a much higher bioavailability, notably on the skin.

EXAMPLE 2

Preparation of Avocado Sugar Hydrosoluble Extract 50 kg fresh avocado, Hass variety, are cut into thin slices, 2-5 mm thick, stone included, with a disk cutting machine. The drying apparatus is a hot air flow thermoregulated oven. Once cut the avocados are distributed into 4-5 cm thick layers onto trays which are laid out in tiers. Drying temperature is set at 80° C. for a total duration of 48 hours. One dried the fruits are exposed to cold pressure. This operation is carried out on a small Komet® laboratory press.

The 4 kg delipidated pieces of fruit (cake) are then ground at a cold temperature then extracted with reflux, in the presence of 25 liters of ethanol. The powder, with the lipids exhausted, is then collected by filtration onto a Büchner funnel, and dried in the oven at 50° C. during 5 hours.

The cake is then washed with demineralised water (10 l), then separated by centrifugation. The soluble fraction (liquid) is taken up in order to be purified and concentrated according to the following process:
 Demineralisation with ion exchange resins: demineralisation of heptuloses by passing onto OH⁻, then H⁺ resin.
 Ultrafiltration on 10,000 Da: ultrafiltration is carried out using a system which is equipped with 4 membranes having a cut-off limit of 10 kDa.
 Vacuum concentration: concentration of the purified extract is carried out with a vacuum evaporator until dry matter at about 4% is obtained.
 Packaging: concentration of the extract is adjusted at 5% dry matter and a preservative is added, then a sterile filtration is carried out with a 0.2 μm cut-off limit membrane, and the product is packed.

The following Table 7 shows the composition of the C7 avocado sugar extract, at 5% dry matter, as prepared according to the here above described process:

TABLE 7

| Appearance | Pale yellow coloured solution |
|---|---|
| Analytic criteria | |
| Dry matter | 5% |
| pH value (¼ dilution) | 7.0 |
| Absorbance at 420 nm (¼ dilution) | 0.013 |
| Absorbance at 550 nm (¼ dilution) | 0.003 |
| Composition (% dry matter) | |
| Sucrose | 3.0 |
| Glucose | 7.5 |
| D-mannoheptulose | 40.0 |
| Fructose | 10.6 |
| Perseitol | 28.8 |

EXAMPLE 3

Induction of Beta-Defensin-2 with the Avocado Peptide Extract

Cell Seeding (J0):
 Normal human keratinocytes are seeded in 96 well plates (about 20,000 cells/well), in the presence of a specific medium which is enriched in calcium (final concentration 1.3 mM), as formerly described in the publication "Human β-Defensin-2 production in Keratinocytes is regulated by Interleukin-1, Bacteria, and the State of Differentiation", Alice Y. Liu et al., The Society for Investigative Dermatology, vol. 118, No 2, February 2002, pages 275-281.
Cell Processing (J1):
 After incubation for 24 hours at 37° C., 5% $CO_2$:
  => 2 rinses with 200 μl/well PBS (phosphate buffer in saline solution)=
  => cell stimulation with 200 μl/well (in medium supplemented with $Ca^{++}$):
   avocado peptide extract at concentrations of 3, 1 and 0.3%, or, respectively, 0.15, 0.05 and 0.015% dry matter
   Il-1β at a concentration of 100 ng/ml (positive induction checking for hBD-2)
End of Processing (J2): ELISA
 After 24 hours incubation, the induction of hBD-2 is assessed with an ELISA technique using a specific antibody (goat polyclonal to human BD2; Abcam; ab9871).

The obtained results are summarised in the following Table 8:

TABLE 8

| | Control cells | Positive control (IL-1β) | Avocado peptide extract (0.3%) | Avocado peptide extract (1%) | Avocado peptide extract (3%) |
|---|---|---|---|---|---|
| hBD-2 (OD) | 0.03 | 0.103 | 0.057 | 0.047 | 0.05 |
| hBD-2 (OD) | 0.036 | 0.11 | 0.056 | 0.056 | 0.063 |
| hBD-2 (OD) | 0.036 | 0.105 | 0.062 | 0.054 | 0.072 |
| Average | 0.034 | 0.106 | 0.058 | 0.052 | 0.062 |

It may be observed that, in a quite unexpected manner, the inventive avocado peptide extract allows one to increase the amount of hBD-2 which is produced.

EXAMPLE 4

Induction of mRNAs which Code for hBD-2 and for Antimicrobial Like Peptides (Elastase Specific Inhibitor)

The 'cDNA micro array' method was used to study the effects of avocado peptide extracts on the expression of genes which code for structural and regulatory proteins which might be of interest in skin physiology. Such an approach allows one to screen in a single step the effects of a product or of a treatment on the expression of genes in a given biological system, and to obtain a 'signature' of the effects of this treatment.

Conditions of Culture and Assayed Products

The avocado peptide extracts, at concentrations of 3, 1 and 0.3%, or, respectively, 0.15, 0.05 and 0.015% dry matter, as obtained by the inventive process, were directly incubated in the culture medium for reconstructed epidermis, Skinethic®, during 24 hours.

Analysis of Gene Differential Expression

The approach used, which is recommended by Clontech (Palo Alto, USA), comprises:
  A total RNA extraction and purification step
  A messenger RNA purification step according to the AtlasPure protocol (Clontech)
  A labelling of DNA probes with $P^{32}$ using reverse transcription
  A purification of probes as labelled by exclusion column chromatography, and checking of the quality and equivalence by liquid scintillation counting.
  A hybridization of membranes (Custom ATLAS BIOAlternative) with the radiolabelled probes (68° C., overnight).

Results

The effects on the synthesis of mRNAs coding for antimicrobial peptides (hBD-2) and antimicrobial like peptides (Elastase specific inhibitor/SKALP/elafin) are shown in the following Table 9:

TABLE 9

| Genes | Avocado peptide extract, pure active (0.015%) | Avocado peptide extract, pure active (0.05%) | Avocado peptide extract, pure active (0.15%) |
|---|---|---|---|
| Beta defensin 2 | 16.1 | 69.7 | 103.9 |
| Specific Elastabase Inhibitor | 5.5 | 14.7 | 13.5 |

EXAMPLE 5

Tolerance

All the studies were conducted on avocado peptide extract disclosed in Example 1, generally at the 0.05% DM (dry matter) and the 0.005% DM doses.

A. Skin Tolerance

Cytotoxicity on Keratinocytes:

A cytotoxicity test was performed on normal human keratinocytes.

After 24 hours and 48 hours of avocado peptide extract treatment, an MTT viability test was conducted.

Avocado peptide extract does not induce cytotoxicity up to the 0.2% DM dose inclusive.

Inflammation:

The pro-inflammatory potential of avocado peptide extract was evaluated on normal human keratinocytes.

After treating the keratinocytes with avocado peptide extract for 24 or 48 hours, interleukin-1β (IL1β) and Tumour Necrosis Factor α (TNF-α), two early inflammation mediators, were assayed in the cell supernatant.

At 0.005%, 0.05% and 0.1% DM concentrations, avocado peptide extract does not induce the release of IL1β or TNFα; therefore, avocado peptide extract is not pro-inflammatory.

B. Ocular Tolerance

The ocular tolerance potential of avocado peptide extract was evaluated using the official neutral red release method on rabbit cornea fibroblasts (SIRC line).

The avocado peptide extract was tested in a 2% solution.

With an LD50 (Concentration giving 50% mortality) of 743%, avocado peptide extract is classified under "Negligible cytotoxicity", which corresponds to the class with the best tolerance.

This class is equivalent to the "Mild irritant" class as per the Draize test.

EXAMPLE 6

Retinoids Like Activities

In order to demonstrate the 'retinoid-class' response profile for avocado peptide extract, micro-assay screening was conducted.

1. Materials and Methods.

The avocado peptide extract disclosed in Example 1 were used.

Seventeen day old Skinethic reconstructed epidermises were treated systemically with 0.04% DM avocado peptide extract, 1 µM retinoic acid [Sigma] (positive reference) for 6 hours and 24 hours.

The gene expression analysis conducted using standard simplified DNA arrays. These mini-chips were produced on a Nylon substrate, spotting specific cDNA of the markers of interest.

The analysis was conducted using proprietary optimised miniaturised technology, based on the use of messenger RNA and $^{33}P$ labelling:

At the end of each culture time, the epidermises were rinsed with a PBS solution. The total RNA in the epidermises was then extracted and purified using Tri-Reagent [Sigma] according to a standardised protocol. The quantity and quality of the RNA were then evaluated using an Agilent 2001 bioanalyser.

The mRNA from each culture was then reverse transcribed using oligodT and a deoxyribonucleotide triphosphate labelled with $^{33}P$. Multiple cDNA 'target' labelled sequences were produced for each culture. These targets were then hybridised, under optimised conditions, with the excess 'probe' cDNA fixed on the membranes. After washing, the relative quantity of labelled target was detected by means of direct counting on PhosphorImager.

The membrane analysis was conducted using ImageQuant TL software [Image Analysis, Amersham Biosciences]. The data processed demonstrate the differential expression of the various genes following avocado peptide extract treatment compared to the corresponding reference.

The most significant results of the screening are given in Table 10:

| | % variation with respect to reference | | | |
|---|---|---|---|---|
| | 1 µM retinoic acid | | 0.04% Avocado Peptide Extract | |
| | 6 hours | 24 hours | 6 hours | 24 hours |
| Desmoglein 1 | −40% | −95% | −15% | −35% |
| NICE-1 protein | −3% | +217% | −12% | +46% |

-continued

| | % variation with respect to reference | | | |
|---|---|---|---|---|
| | 1 µM retinoic acid | | 0.04% Avocado Peptide Extract | |
| | 6 hours | 24 hours | 6 hours | 24 hours |
| S100 A7 | +118% | +3240% | +17% | +61% |
| S100 A8 | +34% | +1347% | −34% | +260% |
| S100 A9 | +83% | +552% | −47% | +322% |
| SPRL6A (epidermal differentiation complex protein like protein) | −41% −16% | +202% −31% | −14% +15% | +123% +48% |
| Elafin | +13% | −22% | +83% | +24% |
| Lysyl oxidase like 2 (LOXL2) | −16% | −16% | +48% | / |
| Heme oxygenase 1 | −17% | +108% | −7% | +60% |
| Thioredoxin | −26% | +126% | / | +54% |

This screening demonstrated a "retinoid-like" response profile for avocado peptide extract. In fact, similar to retinoic acid, avocado peptide extract has an action on keratinocytes differentiation markers (↘ desmoglein 1, ↗ NICE-1, ↗ S100 proteins, ↗ SPRR).

Moreover the screening demonstrates the action of avocado peptide extract on the gene expression of other markers of interest:
- ↗ heme oxygenase 1, ↗ thioredoxin which appear to indicate an anti-oxydant potential to be confirmed,
- ↗ elafin, ↗ LOXL2, targets which may be of interest in anti-ageing (dermal extracellular matrix protection).

EXAMPLE 7

Effect on Skin Cell Proliferation

1. Introduction

The micro-array screening results demonstrated a "retinoid-like" response profile for avocado peptide extract.

Retinoid-like molecules, such as retinol, retinal or retinoic acid, are more specifically (but not only) used in anti-ageing treatments.

In order to evaluate the anti-ageing activity of avocado peptide extract, we firstly analysed their effect on epidermal keratinocyte and dermal fibroblast cell proliferation.

In fact, cell proliferation indicates cell regeneration, an important stage in combating ageing; particularly as skin ageing is accompanied by a slowing down in cell proliferation, as demonstrated by the morphometric evaluation of the number of epidermal layers and dermal fibroblasts. In addition, fibroblast proliferation activation stimulates the dermal metabolism and promotes the neosynthesis of essential extracellular matrix macromolecules such as collagen, elastin, etc.

The cell proliferation was evaluated using a neutral red incorporation tests. This test is based on the ability of living cells to incorporate and fix neutral red, a supravital staining agent. Therefore, the staining activity intensity (optical density measurement of cell lysates) reflects the quantity of living cells.

2. Materials and Method

Avocado Peptide Extract: as Disclosed in Example 1.

Cell Models:

Normal human epidermal keratinocytes (NHEK), supplied by Cambrex, were cultured in KGM2 culture medium [Cambrex]. Normal human dermal fibroblasts (NHDF), supplied by Cambrex, were cultured in RPMI 1640 medium with GlutaMAX I [Invitrogen] supplemented with 1% or 10% fetal calf serum [FCS, Invitrogen].

Method:

The cells were inoculated in 96-well plates in KGM2 medium for the NHEK and in RPMI medium with 1% FCS for the NHDF.

After 24 hours of incubation at 37° C., 5% $CO_2$, the cells were treated for 48 hours with 0.005% or 0.05% DM avocado peptide extract or with 1 µM retinoic acid [Sigma] (positive reference) in KGM2 medium for the NHEK or in RPMI medium with 1% FCS for the NHDF.

An additional condition was conducted for the NHDF: treatment with complete medium (RPMI with 10% FCS: optimal conditions for NHDF proliferation).

At the end of treatment, the quantity of cells per well was evaluated by means of a neutral red incorporation test:

After 3 hours in contact with neutral red, the cells were rinsed and lysed and the optical density proportional to the quantity of living cells was read at 540 nm against the blank (well with no cells).

3. Results

Avocado peptide extract activates keratinocyte proliferation significantly at 0.005% DM (+38% proliferation) and 0.05% DM (34% proliferation) (Table 11). In addition, this effect is comparable to that of retinoic acid (+36%) used as the reference in the test.

TABLE 11

| NHEK proliferation | | |
|---|---|---|
| | Neutral Red (OD 540) | % |
| Control cells | 0.5215 ± 0.0992 | — |
| Positive reference (retinoic acid) | 0.6981 ± 0.1627* | +36 |
| 0.005% DM avocado peptide extract | 0.7067 ± 0.0955** | +38 |
| 0.05% DM avocado peptide extract | 0.6886 ± 0.1733** | +34 |

*$p < 0.05$ - student's test
**$p < 0.01$ - student's test

Avocado peptide extract activates fibroblast proliferation significantly at 0.005% DM (+21% proliferation) and 0.05% DM (+15% proliferation) comparably to retinoic acid (+20%), the positive reference of the test.

TABLE 12

| NHDF proliferation | | |
|---|---|---|
| | Neutral Red (OD 540) | % |
| Control cells | 0.1607 ± 0.0141 | — |
| Positive control (complete medium) | 0.30183 ± 0.02657** | +87 |
| Positive reference (retinoic acid) | 0.19233 ± 0.00765** | +20 |
| 0.005% DM avocado peptide extract | 0.19533 ± 0.01383** | +21 |
| 0.05% DM avocado peptide extract | 0.18567 ± 0.00591** | +15 |

**$p < 0.01$ - student's test

EXAMPLE 8

Hydrating and Relipiding Activity

1. Effect on Glycosaminoglycan (GAG) and Hyaluronic Acid Synthesis by Keratinocytes (Hydrating Activity)

Materials and Method:

Normal human epidermal keratinocytes (NHEK) were pre-cultured for 24 hours at 37° C., 5% $CO_2$ in calcium-depleted (0.09 mM) SFM medium [Invitrogen] supplemented with 0.25 ng/ml EGF [Invitrogen], 25 µg/ml pituitary extract [Invitrogen] and 25 µg/ml gentamycin [Sigma].

The keratinocytes were then treated for 72 hours with 0.05% DM and 0.005% DM avocado peptide extract (Example 1) or with the references: 0.1 µM retinoic acid [Sigma] or 1.5 mM calcium [Prolabo]. Two identical runs were prepared to assay, on one hand, hyaluronic acid release/production and, on the other, sulphide incorporation in the GAG fraction. The group corresponding to the GAG assay was supplemented with $^{35}$S-sulphate [Amersham] after 48 hours of culture (labelling for the last 24 hours).

At the end of the treatment, in the group corresponding to the GAG assay, the incorporated radioactivity was counted and thus the variation in GAG synthesis with respect to the analysed control.

In the group corresponding to the hyaluronic acid assay, at the end of treatment, the culture supernatants were sampled and the hyaluronic acid assayed using a specific modified ELISA test [Biogenic].

The between-group comparisons were conducted by means of an analysis of variance using the Dunnett multiple comparison test.

Results:

Effect on GAG Synthesis:

Calcium, used as the reference (pro-differentiating effect) stimulates $^{35}$S-sulphate incorporation in the GAG fraction; this result validates the test.

Retinoic acid treatment does not modify GAG synthesis by keratinocytes significantly.

Avocado peptide extract induces a significant increase in GAG synthesis (+30%) (Table 13).

TABLE 13

| GAG synthesis by keratinocytes | | |
|---|---|---|
| | 35-5 sulphate incorporation (cpm) | % |
| Control cells | 11163 ± 1138 | — |
| Calcium | 17753 ± 876** | +59 |
| Retinoic acid | 13217 ± 421 | +18 |
| 0.005% DM avocado peptide extract | 14973 ± 2916* | +34 |
| 0.05% DM avocado peptide extract | 14833 ± 281 | +33 |

*p < 0.05 - Dunnett test
**p < 0.01 - Dunnett test

Effect on Hyaluronic Acid Synthesis/Release:

Retinoic acid, the test reference, increases the quantity of hyaluronic acid found in the keratinocyte culture supernatants significantly. Without having an effect on GAG synthesis, retinoic acid specifically stimulates hyaluronic acid production.

0.005% avocado peptide extract increase hyaluronic acid production significantly (+30%) (Table 14).

TABLE 14

| Hyaluronic acid synthesis/release by keratinocytes | | |
|---|---|---|
| | HA (mg/ml) | % |
| Control cells | 4684 ± 376 | — |
| Retinoic acid | 11503 ± 457** | +146 |
| 0.005% DM avocado peptide extract | 6138 ± 958* | +31 |

TABLE 14-continued

| Hyaluronic acid synthesis/release by keratinocytes | | |
|---|---|---|
| | HA (mg/ml) | % |
| 0.05% DM avocado peptide extract | 4924 ± 447 | +5 |

*p < 0.05 - Dunnett test
**p < 0.01 - Dunnett test

2. Effect on Epidermal Lipid Neosynthesis (Relipidising Activity)

Materials:

Reconstructed epidermises at D5 [BIOalternatives] were cultured under the following conditions:
- Reference epidermises (R): differentiation medium [BIOalternatives],
- Standard epidermises (T): depleted differentiation medium,
- 0.005% DM and 0.05% DM avocado peptide extract (Example 1) in depleted differentiation medium (systemic application).

Method:

The epidermises were placed in 12-well plates under the conditions described above (depleted differentiation medium or not, containing avocado peptides or not).

After 24 hours, the culture medium was replenished and supplemented with 0.75 µCi/ml of $^{14}$C-acetate [Amersham]. The epidermises were then incubated for 48 hours at 37° C. and 5% $CO_2$.

At the end of the treatment time, the epidermises were washed with PBS [Invitrogen], dissociated from their boats and lysed with 0.5 M perchloric acid on ice.

The lipids were then extracted with a methanol/chloroform solution (2:1). The incorporated radioactivity (corresponding to the total lipids) was then quantified by means of liquid scintillation. After thin-layer chromatography, the lipids were analysed separately by means of direct input of the radioactivity of the various spots and quantification using a Cyclone type phosphorimager [Packard].

Results:

Effect on Total Lipid Synthesis:

The complete differentiation medium (R epidermises) induces a non-significant increase of the incorporation of acetate in the total lipids.

Avocado peptide extract does not affect total lipid synthesis (Table 15).

TABLE 15

| Total lipid synthesis on reconstructed epidermises | | |
|---|---|---|
| | Acetate Incorporation (cpm) | % |
| T epidermises (depleted medium) | 32 171 ± 1 821 | — |
| R epidermises (differentiation medium) | 41 143 ± 6 715 (NS) | +28 |
| 0.005% DM avocado peptide extract | 34 705 ± 1 112 (NS) | +11 |
| 0.05% DM avocado peptide extract | 35 588 ± 3 004 (NS) | +8 |

NS = non significant difference

Lipid Neosynthesis Profile Analysis (Tables 16 and 17):

Complete differentiation medium (R epidermises) induces a modification of the phospholipid profile with, in particular, an increase in phospholipids (+24% compared to T epidermises), cholesterol sulphate (+13%). The total quantity of ceramides/cerebrosides is not modified; however, a significant modification in the lipid profiles obtained is observed: increase in the most polar ceramides/cerebrosides (+38%) and decrease in the least polar ceramides/cerebrosides (Table 16). With respect to neutral lipids, complete differentiation medium induces an increase in cholesterol (+19%), free fatty acids (+37%) and a decrease in esterified fatty acids (−38%) (Table 17).

0.005% and 0.05% DM avocado peptide extract induce an increase in the most polar ceramides/cerebrosides (+30% and +28% compared to T epidermises), a decrease in the least polar ceramides/cerebrosides (−14% and 17%) (Table 16) and 0.05% avocado peptides induce an increase in free fatty acids (+32%) (Table 17). These effects are similar to those of the complete differentiation medium.

TABLE 16

Lipid profiles in "phospholipids + sphingolipids" system (% of T standard)

| | Sphingo-myelin | Phospho-lipids | Cholesterol sulphate | Polar ceramides/ cerebrosides | Less polar ceramides/ cerebrosides |
|---|---|---|---|---|---|
| T epidermises (depleted medium) | 100 | 100 | 100 | 100 | 100 |
| R epidermises (differentiation medium) | 105 | 124 | 113 | 138 | 84 |
| 0.005% DM avocado peptide extract | 90 | 104 | 101 | 130 | 86 |
| 0.05% DM avocado peptide extract | 91 | 112 | 105 | 128 | 83 |

TABLE 17

Lipid profiles in "neutral lipids + fatty acids" system (% of T standard)

| | Cholesterol | Free fatty acids | Esterified fattyacids |
|---|---|---|---|
| T epidermises (depleted medium) | 100 | 100 | 100 |
| R epidermises (differentiation medium) | 119 | 137 | 62 |
| 0.0050% DM avocado peptide extract | 112 | 103 | 93 |
| 0.05% DM avocado peptide extract | 107 | 132 | 90 |

EXAMPLE 9

Activity on Dermal Extracellular Matrix

1. Materials and Method

Normal human dermal fibroblast were inoculated in 6-well plates in RPMI 1640 medium with GlutaMAX I [Invitrogen] supplemented with 10% fetal calf serum [FCS, Invitrogen].

Cell Treatment for Collagen I, Elastin, LOX and LOXL Expression Study:

After 24 hours of incubation at 37° C., 5% $CO_2$, the fibroblasts were treated with 5 ng/ml TGFβ1 (positive control) [R&D Systems] or with 0.0050% DM and 0.05% DM avocado peptide extract (Example 1) in RPMI medium with 1% FCS. The cells were then incubated at 37° C., 5% $CO_2$ for 24 hours for the collagen I and elastin study or 48 hours for the LOX and LOXL study.

Cell Treatment for MMP1 Expression Study:

After 6 hours of incubation at 37° C., 5% $CO_2$, the fibroblasts were pre-treated with 1 ng/ml TGFβ1 (reference) [R&D Systems] or with 0.005% DM and 0.05% DM avocado peptide extract (Example 1) in RPMI medium without FCS.

After 16 hours of incubation, the fibroblasts were stimulated for 2 hours with 10 nM PMA (Phorbol Myristate Acetate) [Sigma] in RPMI medium without FCS.

At the end of the treatments, the culture supernatants were removed and the total RNA extracted using the RNeasy Mini-Kit [Qiagen] extraction kit. The total RNA was then assayed with mini-chips using the Experion™ system and the Experion RNA StdSens kit [Biorad] and reverse-transcribed to cDNA using the iScript cDNA Synthesis kit [Biorad].

The neo-synthesised cDNA relating to the genes of interest (Collagen I, Elastin, MMP1, LOX or LOXL) or the reference genes were amplified selectively by means of real-time PCR on iQ5 [Biorad] using SybrGreen technology [iQ SybrGreen kit, Biorad].

The real-time RT-PCR method enables the relative quantification of the level of expression of the gene of interest with respect to that of a reference gene in response to a given treatment.

The quantitative analysis of the results is based on the compilation of the threshold cycles (or Ct).

The threshold cycle corresponds to the point where the fluorescence emission signal is statistically and significantly higher than the background noise. The threshold cycle is directly correlated with the number of initial copies of the target DNA.

For each sample, the level of expression of the gene of interest was standardised by the level of expression of the most stable reference gene. The most stable reference gene was determined using the GeNorm macro, it consists of the HPRT gene for the study of the expression of collagen I, elastin, LOX and LOXL and the YWHAZ gene for the study of the expression of MMP1.

The ΔCt value is calculated as follows:

$$\Delta Ct = Ct_{target\ gene} - Ct_{reference\ gene}$$

The ΔCt values were compared in a statistical test (Student's t test) in order to evaluate the significance of the results obtained.

In a second stage, the variation, as a function of the treatment, of the number of copies of the gene of interest was determined. The ΔΔCt value is calculated as follows:

$$\Delta\Delta Ct = \Delta Ct_{control} - \Delta Ct_{treated}$$

Finally, the relative quantity (RQ) is calculated: $RQ=(1+E)^{\Delta\Delta Ct}$.

E (efficiency) is considered to be equal to 1; this gives:

$$RQ = 2\Delta\Delta^{Ct}$$

For the study of the expression of MMP1, the inhibition percentage was calculated as follows:

$$\frac{100 - RQ_{treated\ cells}}{RQ_{stimulated\ cells}} \times 100$$

2. Results

Effect on Gene Expression of Type I Collagen:

After 24 hours of treatment, TFGβ1, the positive control, stimulates the gene expression of type I collagen in fibroblasts significantly (74% increase); this result validates the test.

0.05% DM avocado peptide extract stimulate the gene expression of type I collagen significantly in fibroblasts (44% increase) (Table 18).

TABLE 18

Gene expression of Collagen I in fibroblasts

| | Relative quantity standardised with HPRT |
|---|---|
| Control cells | 1.00 |
| 5 mg/ml TGF b1 | 1.74* |
| 0.005% DM avocado peptide extract | 0.98 |
| 0.05% DM avocado peptide extract | 1.44** |

*$p < 0.05$ - Student's test
**$p < 0.01$ - Student's test

Effect on Gene Expression of Elastin:

After 24 hours of treatment, TFGβ1, positive control, stimulates the gene expression of elastin in fibroblasts (59% increase).

0.05% DM avocado peptide extract stimulate the gene expression of elastin significantly in fibroblasts (78% increase) (Table 19).

TABLE 19

Gene expression of Elastin in fibroblasts

| | Relative quantity standardised with HPRT |
|---|---|
| Control cells | 1.00 |
| 5 mg/ml TGF b1 | 1.59 |
| 0.005% DM avocado peptide extract | 1.06 |
| 0.05% DM avocado peptide extract | 1.78** |

**$p < 0.01$ - Student's test

Effect on Gene Expression of MMP-1:

Fibroblast stimulation by PMA for 2 hours induces a significant increase in the gene expression of MMP1 (+81%).

Pre-treatment with 1 ng/ml TGFβ1 (reference molecule) induces a significant inhibition (−66%) of the gene expression of MMP1 induced by the PMA treatment. This result validates the test (Table 20).

Avocado peptide extract in pre-treatment for 16 hours makes it possible to inhibit the gene expression of MMP1 induced by PMA. This inhibition is significant for the 0.05% DM concentration (−59%) (Table 20).

TABLE 20

Gene expression of MMP1 in fibroblasts

| | Relative quantity standardised with YWHA2 | Inhibition (% vs stimulated cells) |
|---|---|---|
| Control cells | 1.00 | — |
| Stimulated cells (10 nM PMA) | 1.81** | — |
| Reference (1 mg/ml TGF b1) | 0.61 | −66 $$ |
| 0.005% DM avocado peptide extract | 1.42 | −21 |
| 0.05% DM avocado peptide extract | 0.75 | −59 $ |

**$p < 0.01$ - Student's test with respect to control cells
$ $p < 0.05$
$$ $p < 0.01$ - Student's test with respect to stimulated cells Effect on Gene Expression of Lysyl Oxidases LOX and LOXL After 48 hours of treatment, 0.005% DM and 0.05% DM avocado peptide extract induce a significant increase in the gene expression of lysyl oxidase LOX in fibroblasts (25% increase) (Table 21).

TABLE 21

Gene expression of LOX in fibroblasts

| | Relative quantity standardised with HPRT |
|---|---|
| Controls cells | 1.00 |
| 0.005% DM avocado peptide extract | 1.25** |
| 0.05% DM avocado peptide extract | 1.25** |

**$p < 0.01$ - Student's test

After 48 hours of treatment, 0.005% DM avocado peptide extract induce a significant increase in the gene expression of lysyl oxidase-like LOXL in fibroblasts (22% increase) (Table 22). At 0.05% DM, this increase is not significant.

TABLE 22

Gene expression of LOXL in fibroblasts

| | Relative quantity standardised with HPRT |
|---|---|
| Controls cells | 1.00 |
| 0.005% DM avocado peptide extract | 1.22* |
| 0.05% DM avocado peptide extract | 1.15 |

*$p < 0.05$ - Student's test

EXAMPLE 10

Activity on Mast Cell: Implication for Photo-aged Skin Treatment

1. Materials and Methods

Rat peritoneal mast cells ($2.10^5$ cells/ml) were incubated for 30 minutes at 37° C. in the presence or not of 0.005% DM and 0.05% DM avocado peptide extract (Example 1) or 50 μM Quercetin [Sigma] (reference tryptase release inhibitory molecule).

The cells were then stimulated for 15 minutes by 0.5 μM calcium ionophore A23187 [Millipore] to induce the release of tryptase.

The reaction was stopped by means of centrifugation at 4° C. The tryptase was assayed in the pellets and in the supernatants by means of a commercial kit [Millipore] based on the spectrophotometric detection of the chromophore p-nitroaniline (pNA) after cleavage of the substrate tosyl-gly-pro-lys-pNA by tryptase.

2. Results

Quercetin significantly inhibits tryptase release by mast cells induced by calcium ionophore (−47%, Table 23).

0.005% DM avocado peptide extract significantly inhibit tryptase release by mast cells stimulated with calcium ionophore A23187 (−30%, Table 23).

TABLE 23

Effect of avocado peptide extract on tryptase release by mast cells

|  | Tryptase (mg/ml) | Inhibition (% vs stimulated cells) |
|---|---|---|
| Control cells | 2 ± 1 | — |
| Stimulated cells (Ca ionophore) | 83 ± 5 | — |
| Ca ionophore + 50 μM Quercetin | 44 ± 2** | −47 |
| Ca ionophore + 0.005 DM avocado peptide extract | 58 ± 7** | −30 |
| Ca ionophore + 0.05 DM avocado peptide extract | 93 ± 10 | — |

**p < 0.01 - Student's test with respect to stimulated cells

EXAMPLE 11

Anti-age Activity: Antioxidant and Protective Potential in a Senescence Model

1. Anti-radical Activity of Avocado Peptide Extract

Materials and Method:

The anti-radical activity of avocado peptide extract (Example 1) was studied in Jurkat cell line (human lymphoid cells) cultures. The relative lipid peroxide content inside the cells was measured in the basal state and following hydrogen peroxide treatment ($H_2O_2$, radical species production stimulation).

This measurement was made using a specific fluorescent probe selected and quantified by means of flow cytometry. This technique offers the advantage of very high specificity by measuring the fluorescence of individual cells, on a large number of cells (10,000 cells analysed per sample).

The cells were prepared in phenol red-free DMEM medium [Merck] with 1.87 mg/ml sodium bicarbonate [Invitrogen] according to the following conditions:
  cells treated with $H_2O_2$ with the C11-fluorine probe (to quantify lipid peroxides);
  cells not treated with $H_2O_2$ with C11-fluorine probe.

The probe was incorporated in the cells and the cells were then washed and incubated in the presence or not (standard) of 0.05%, 0.1%, 0.2% and 1% DM avocado peptides or 100 μM BHA (Butylated hydroxyanisole) [Sigma] (reference antioxidant) and in the presence or not of 10 μM $H_2O_2$ for 30 minutes at 37° C. and 5% $CO_2$.

In the presence of hydrogen peroxide, the C11-fluorine probe integrated in the membranes is oxidised and its fluorescence decreases. Therefore, a decrease in the fluorescence signal conveys an increase in the membrane lipid peroxide content (and conversely).

The between-group comparisons were conducted using the Student's test and the protection percentage (P) was calculated as follows:

$$P\% = 100 - \frac{(\text{Standard} + H_2O_2 - \text{Treated} + H_2O_2) \times 100}{\text{Standard} + H_2O_2 - \text{Treated} + H_2O_2}$$

Results:

Avocado peptide extract, from the lowest concentration, protect cells against oxidative stress induced by hydrogen peroxide by reducing lipid peroxide formation (Table 24) significantly, in a comparable way to the reference antioxidant (BHA).

TABLE 24

Relative intracellular quantity of lipid peroxides

|  | % of "oxidised cell" standard | Protection % |
|---|---|---|
| Control cells | 77 | — |
| Standard (cells treated with $H_2O_2$) | 100 | — |
| Reference (100 μM BHA) | 89** | 50 |
| 0.05% DM avocado peptide extract | 85** | 64 |
| 0.1% DM avocado peptide extract | 83** | 74 |
| 0.2% DM avocado peptide extract | 82** | 80 |
| 1% DM avocado peptide extract | 83** | 75 |

**p < 0.01 - Student's test

2. Activity on Oxidised Protein Repair or Elimination Mechanisms

Cell Material:

Normal human dermal fibroblasts were used in this study.

For the tests under basal conditions, the fibroblasts from a young subject (28 years) were used at low passage (<20 population doublings), referred to as "young cells".

For tests under senescence conditions, these "young cells" were brought to senescence by means of successive replications (>37 population doublings), referred to as "senescent cells".

Method:

"Young" or "senescent" normal human dermal fibroblasts were inoculated in 6-well plates with RPMI 1640 medium with GlutaMAX I [Invitrogen] supplemented with 10% fetal calf serum [FCS, Invitrogen].

After 24 hours of incubation at 37° C. and 5% $CO_2$, the cells were treated with 0.005% or 0.05% DM avocado peptide extract for 24 hours or 48 hours.

At the end of treatment, the culture supernatants were removed and the total RNA extracted using the RNeasy Mini-Kit extraction kit [Qiagen]. The total RNA was then assayed in mini-chips using the Experion™ system and the Experion RNA StdSens kit [Biorad] and reverse-transcribed to cDNA using the iScript cDNA Synthesis kit [Biorad].

The neo-synthesised cDNA relating to the genes of interest (p21=senescence marker; thioredoxin; proteasome subunit β1) or the reference genes were amplified selectively by means of real-time PCR on iQ5 [Biorad] using SybrGreen technology [iQ SybrGreen kit, Biorad].

The real-time RT-PCR method enables the relative quantification of the level of expression of the gene of interest with respect to that of a reference gene in response to a given treatment.

The quantitative analysis of the results is based on the compilation of the threshold cycles (or Ct).

The threshold cycle corresponds to the point where the fluorescence emission signal is statistically and significantly higher than the background noise. The threshold cycle is directly correlated with the number of initial copies of the target DNA.

For each sample, the level of expression of the gene of interest was standardised by the level of expression of the most stable reference gene, determined using the GeNorm macro, in this case, it was the YWHAZ gene.

The ΔCt value is calculated as follows:

$$\Delta Ct = Ct_{target\ gene} - Ct_{reference\ gene}$$

The ΔCt values were compared in a statistical test (Student's t test) in order to evaluate the significance of the results obtained.

In a second stage, the variation, as a function of the treatment, of the number of copies of the gene of interest was determined. The ΔΔCt value is calculated as follows:

$$\Delta\Delta Ct = \Delta Ct_{control} - \Delta Ct_{treated}$$

Finally, the relative quantity (RQ) is calculated: $RQ = (1+E)^{\Delta\Delta Ct}$.

E (efficiency) is considered to be equal to 1; this gives:

$$RQ = 2^{\Delta\Delta Ct}$$

Results

Effect on Gene Expression of Thioredoxin:

Avocado peptide extract stimulates the gene expression of thioredoxin significantly in fibroblasts under normal conditions ("young cells"): 48 hours of treatment by 0.005% DM or 0.05% DM avocado peptide extract induce a significant increase of thioredoxin expression of 117% and 87%, respectively (Table 25).

TABLE 25

Gene expression of thioredoxin

|  | Relative quantity standardised with YWHAZ |
| --- | --- |
| Control cells | 1.00 |
| 0.005% DM avocado peptide extract | 2.77** |
| 0.05% DM avocado peptide extract | 1.87* |

*p < 0.05 - Student's test
**p < 0.01 - Student's test

Senescence Model Validation

The fibroblasts were brought to senescence by means of successive replications. The state of senescence obtained in this way was tested by studying the gene expression of p21, a senescence marker.

In this way, as demonstrated in Table 26, the gene expression of p21 is increased in fibroblasts brought to senescence by means of successive replications (>37 population doublings; "senescent cells") as compared to the same cells with less replications (<20 population doublings; "young cells"): 173% increase of p21 after 24 hours of culture and 254% increase of p21 after 48 hours of culture. Therefore, the senescence induction model is validated.

TABLE 26

Gene expression of p21

|  | Relative quantity standardised with YWHAZ | |
| --- | --- | --- |
|  | 24 hours | 48 hours |
| "young cells" | 1.00 | 1.00 |
| "senescent cells" | 2.73 | 3.54* |

*p < 0.05 - Student's test

Effect on Gene Expression of a Catalytic Proteasome Unit

Under basal conditions (on "young cells"), a 24-hour treatment by 0.005% or 0.05% DM avocado peptide extract increases the gene expression of the proteasome subunit β1 significantly: 16% and 14% increase, respectively (Table 27).

TABLE 27

Gene expression of proteasome subunit β1 in "young cells"

|  | Relative quantity standardised with YWHAZ |
| --- | --- |
| Control cells | 1.00 |
| 0.005% DM avocado peptide extract | 1.16* |
| 0.05% DM avocado peptide extract | 1.14** |

*p < 0.5 - Student's test
**p < 0.01 - Student's test

The senescence state of fibroblasts is accompanied by a decrease in the gene expression of proteasome subunit β1 (−31%) in our model (Table 28), this result is in agreement with that described in the literature.

A 48-hour treatment of "senescent cells" with 0.005% or 0.05% DM avocado peptide extract increases the genic expression of proteasome subunit β1 significantly (48% and 33% increase with respect to non-treated "senescent cells"), and the level of expression is comparable to that of the "young cells" (non-significant difference) (Table 28).

TABLE 28

Gene expression of proteasome subunit β1 under the effect of senescence

|  | Relative quantity standardised with YWHAZ | % |
| --- | --- | --- |
| "young cells" | 1.00 | — |
| "senescent cells" | 0.69* | — |
| "senescent cells" + 0.005% DM avocado peptide extract | 1.03 | +48 $$ |
| "senescent cells" + 0.05% DM avocado peptide extract | 0.96 | +33 $ |

*p < 0.5 - Student's test with respect to "young cells"
$ p < 0.05 - Student's test with respect to non-treated "senescent cells"
$$ p < 0.01 - Student's test with respect to non-treated "senescent cells"

3. Effect on Oxidised Protein Content and Hyaluronic Acid Release in an Aged Dermal Fibroblast Model Biological Model:

The study was conducted on normal human dermal fibroblasts at passage 8 (P8, control conditions) and brought to senescence using two separate methods:
  accelerated ageing by means of successive replications: fibroblasts at passage 16 (P16),
  accelerated ageing by means of $H_2O_2$.

The fibroblasts were cultured in DMEM medium [Invitrogen] supplemented with 2 mM L-glutamine [Invitrogen] and 10% Fetal Calf Serum [FCS, Invitrogen].

Method:

Treatment of Fibroblasts Aged by Means of Replication

The fibroblasts at P8 (control) or at P16 were inoculated in 96-well plates and incubated to sub-confluence; the cells were then treated for 72 hours with 0.005%, 0.05% or 0.1% DM avocado peptide extract (Example 1) or with 150 µM BHA [Butylated hydroxyanisol, Sigma] (reference).

Treatment of Fibroblasts Aged by Means of $H_2O_2$

The fibroblasts (at P8) were inoculated in 96-well plates and incubated to sub-confluence; the cells were then pre-treated for 24 hours with 0.005%, 0.05% or 0.1% DM avocado peptide extract (Example 1) or with 150 µM BHA [Butylated hydroxyanisol, Sigma] (reference).

After this pre-incubation, the cells were incubated for 2 hours in the presence or not ($H_2O_2$-free control) of 0.6 mM hydrogen peroxide ($H_2O_2$).

At the end of this incubation, the cells were treated again with avocado peptide extract or BHA for 168 hours, with retreatment of the cells and a change of medium every 48 hours.

Hyaluronic Acid Assay

At the end of incubation, the hyaluronic acid concentrations were evaluated in the culture supernatants by means of ELISA using a commercial kit [R&D Systems].

Oxidised Protein Labelling

After incubation, the cells were rinsed and fixed with methanol. The fluorescein-5-thiosemicarbazide probe (20 µM) [Invitrogen] was added for 30 minutes at ambient temperature and, in parallel, the cell nuclei were stained with Hoechst [Sigma]. The image acquisition was performed using the INCell Analyzer™ 1000 unit [GE Healthcare], with the ×20 lens.

Oxidised Protein Quantity Measurement by Means of Flow Cytometry

After incubation, the cells were rinsed and fixed with methanol. The fluorescein-5-thiosemicarbazide probe (20 µM) [Invitrogen] was added for 1 hour at ambient temperature. The fluorescence parameters were measured by means of flow cytometry on a population of 10,000 individual cells per sample using the FACSArray cytometer [Becton-Dickinson].

Results:

Effect on Hyaluronic Acid Synthesis in Fibroblasts Aged by Means of Replication or $H_2O_2$ Fibroblasts ageing resulted in a decrease in hyaluronic acid secretion, irrespective of the ageing mode: by means of replication (−37%, Table 29) or $H_2O_2$ treatment (−64%, Table 30).

The BHA reference did not limit the decrease in hyaluronic acid secretion observed with fibroblasts ageing by means of replications (Table 29) or $H_2O_2$ (Table 30). On the contrary, BHA amplified the effect of $H_2O_2$ markedly.

Avocado peptide extract limited the decrease in hyaluronic acid synthesis in fibroblasts aged by means of replication or $H_2O_2$:

In the replication-aged dermal fibroblast model, 0.1% DM avocado peptide extract stimulated hyaluronic acid secretion significantly and made it possible to obtain an equivalent expression level to the control cells (referred to as "young cells") (69% increase, Table 29).

In the $H_2O_2$-aged dermal fibroblast model, 0.005% DM and 0.05% DM avocado peptide extract stimulated hyaluronic acid secretion significantly (43% and 91% increase, respectively, Table 30).

TABLE 29

Effect of avocado peptide extract on hyaluronic acid synthesis in a replication-aged fibroblast model

|  | Hyaluronic acid (µg/ml) | % |
|---|---|---|
| Control cells | 1.14 ± 0.120 | — |
| "senescent cells" (P16) | 0.72 ± 0.06 $ | −37 |
| Reference (150 µM BHA) | 0.67 ± 0.03 | — |
| 0.005% DM avocado peptide extract | 0.7 ± 0.02 | |
| 0.05% DM avocado peptide extract | 0.86 ± 0.06 ns | +21 |
| 0.1% DM avocado peptide extract | 1.21 ± 0.03** | +69 |

$ $p < 0.05$ - Student's test with respect to control cells
** $p < 0.01$ - Student's test with respect to P16 cells

TABLE 30

Effect of avocado peptide extract on hyaluronic acid synthesis in an $H_2O_2$-aged fibroblast model

|  | Hyaluronic acid (µg/ml) | % |
|---|---|---|
| Control cells | 2.58 ± 0.19 | — |
| "senescent cells" ($H_2O_2$) | 0.92 ± 0.08 $$ | −64 |
| Reference (150 µM BHA) | 0.28 ± 0.05** | −70 |
| 0.005% DM avocado peptide extract | 1.32 ± 0.1* | +43 |
| 0.05% DM avocado peptide extract | 1.76 ± 0.11** | +91 |
| 0.1% DM avocado peptide extract | 1.26 ± 0.17 ns | +37 |

$$ $p < 0.01$ - Student's test with respect to control cells
* $p < 0.05$ - Student's test with respect to "senescent cells"
** $p < 0.01$ - Student's test with respect to "senescent cells"

Effect on Oxidised Proteins in Fibroblasts Aged by Means of Replication

Fibroblasts ageing by means of replication induced a non-significant increase in the oxidised protein content (+35%, Table 31).

The BHA reference inhibited this accumulation of oxidised proteins significantly (−57%).

0.005% DM avocado peptide extract significantly inhibited the accumulation of oxidised proteins induced by fibroblast ageing by means of replication (−44%, Table 31).

TABLE 31

Effect of avocado peptide extract on oxidised proteins content in a replication-aged fibroblast model (INCell Analyzer analysis)

|  | Oxidised proteins (cytoplasmic fluorescence intensity/number of cells) | % |
|---|---|---|
| Control cells | 182 563 | — |
| "senescent cells" (P16) | 246 283 ns | +35 |
| Reference (150 µM BHA) | 105 314* | −57 |
| 0.005% DM avocado peptide extract | 138 071* | −44 |
| 0.05% DM avocado peptide extract | 142 059 ns | −42 |
| 0.1% DM avocado peptide extract | 162 540 ns | −34 |

* $p < 0.05$ - Student's test with respect to P16 cells
Effect on oxidised proteins in fibroblasts aged by means of $H_2O_2$ Fibroblasts ageing by means of $H_2O_2$ induced a non-significant increase in the oxidised protein contents (+31%, Table 32).

The BHA reference had no effect on the oxidised protein content.

0.005% DM avocado peptide extract significantly inhibited the accumulation of oxidised proteins induced by fibroblast ageing by means of $H_2O_2$ (−41%, Table 32).

TABLE 32

Effect of avocado peptide extract on oxidised protein content in an $H_2O_2$-aged fibroblast model (Flow cytometry analysis)

|  | Oxidised proteins (fluorescence intensity) | % |
|---|---|---|
| Control cells | 1425 | — |
| "senescent cells" ($H_2O_2$) | 1872 ns | +31 |
| Reference (150 μM BHA) | 1730 | — |
| 0.005% DM avocado peptide extract | 1100** | −41 |
| 0.05% DM avocado peptide extract | 1948 | — |
| 0.1% DM avocado peptide extract | 1675 | — |

**p < 0.01 - Student's test with respect to "senescent cells"

Conclusion of Examples 5 to 11

These different objectivation studies demonstrated the significance of avocado peptide extract in the anti-ageing field.
Dermal Extracellular Matrix Metabolism Activation:

Following micro-array activity screening, a "retinoid-like" response profile was demonstrated. However, it is well-known that retinoids are of major interest in the treatment of various physiological or pathological conditions of the skin including skin ageing.

Therefore, this led to research on the effect of avocado peptide extract in the anti-ageing field and more specifically their effect on the dermal extracellular matrix.

In this way, we demonstrated that avocado peptides activate skin cell proliferation: epidermal keratinocytes and dermal fibroblasts. Therefore, avocado peptides boost cell proliferation which is slowed down during skin ageing.

Moreover, we also demonstrated a beneficial effect of avocado peptide extract on the dermal extracellular matrix constituents liable to be impaired during ageing. Avocado peptide extract stimulates the synthesis of type I collagen and elastin, two dermal macro-molecules involved in skin firmness, resistance and elasticity and the level of which decreases with age. Similarly, avocado peptide extract has an inhibitory effect on MMP1, the matrix metalloproteinase responsible for the degradation of collagen, which is over-expressed in aged skin.

In addition, two slightly less common targets of the dermal extracellular matrix were also investigated: Lysyl Oxidase ((LOX) and Lysyl Oxidase-Like (LOXL). These two enzymes play a role in elastogenesis and also, to a lesser extent, in collagen fibre coupling. Therefore, they are involved in the correct spatial arrangement of elastin and collagen fibres and their expression decreases with age, which would explain the poor cross-linking of elastin in aged skin. Avocado peptide extract activates LOX and LOXL expression, therefore they would help preserve a satisfactory elastin (and collagen) fibre arrangement with age.
Potentially Protective Activity Against Photo-Ageing:

A probable role of mast cell tryptase in dermal matrix degradation during photo-ageing was recently demonstrated. In fact, the number of mast cells (containing tryptase) in the dermis is increased in photo-aged skins. Moreover, it has been demonstrated that tryptase was capable of activating the latent forms of proteases (pro-MMP1, pro-MMP9) involved in matrix constituent degradation, and also of degrading some of these constituents (collagen I, collagen VI) directly.

Avocado peptide extract inhibits the release of tryptase by stimulated mast cells, therefore they could be of particular interest in the treatment of photo-induced skin ageing.
Protection Against Oxidative Stress, Improvement of Oxidised Protein Repair and Elimination System:

Skin ageing is accompanied by an accumulation of oxidised proteins in the skin. These oxidative modifications of proteins impair their biological function and are involved in age-related cell degeneration. This accumulation during ageing would appear to be associated with reactive oxygen species production, poorer antioxidant defences and poorer damaged cell constituent repair and elimination system effectiveness.

The micro-array screening suggested an antioxidant potential of avocado peptide extract. This was confirmed on a cell model in which avocado peptide extract decreased the formation of lipid peroxides induced by oxidative stress ($H_2O_2$).

The oxidised proteins, which are thus impaired, must be eliminated or repaired to prevent them from accumulating in the cell. Enzymatic oxidised protein repair mechanisms, such as thioredoxin, exist. However, if the impairments are too significant, the protein must be eliminated by various systems, the main one being the proteasome. During ageing, a decrease in the proteasome (in quantity and activity) occurs.

We demonstrated that avocado peptide extract stimulates the expression of thioredoxin, the enzyme responsible (among others) for oxidised protein repair.

In addition, avocado peptide extract stimulates the expression of a catalytic subunit (β1) of proteasome in dermal fibroblasts under normal conditions and in senescent dermal fibroblasts. Interestingly, avocado peptide extract restores subunit β1 expression which is inhibited with senescence. In this way, avocado peptide extract would facilitate the treatment (repair/elimination) of oxidised proteins which are deleterious for epidermal and dermal homeostasis.

This was confirmed by supplementary studies demonstrating the ability of avocado peptide extract to limit the accumulation of oxidised proteins induced by fibroblast ageing (in two senescence induction models: by means of replication and by means of $H_2O_2$ treatment).
Hydrating and Relipidising Activity:

In addition to these biological activities, we demonstrated a hydrating and relipidising effect of avocado peptide extract. In fact, avocado peptide extract stimulates the synthesis of glycosaminoglycans and hyaluronic acid, which are involved in maintaining a satisfactory skin hydration level. Also, avocado peptide extract stimulate the neosynthesis of epidermal lipids, involved in the epidermal barrier function.

This gives avocado peptide extract an interest in the treatment of skin ageing, which is frequently accompanied by skin dryness.

Moreover, this hydrating effect of avocado peptide extract has also been demonstrated in artificially aged dermal fibroblasts (by means of replication and by means of $H_2O_2$ treatment). In this way, whereas in aged fibroblasts, the quantity of hyaluronic acid is reduced, avocado peptide extract is capable of modulating this decrease or even restoring a hyaluronic acid level equivalent to that of young cells.

EXAMPLE 12

Cosmetic Formulations Based on Avocado Peptide Extract

Anti-acneic Cream No 1

| Water | QS 100% |
|---|---|
| Isononyl Isononanoate | 7.000 |
| Di-C$_{12-13}$ malate | 7.000 |
| Isocetyl stearate | 5.000 |
| Butylene glycol | 3.000 |
| *Oryza sativa* | 2.500 |
| Avocado peptide extract | 2.000 |
| Dicaprylyl ether | 2.000 |
| Silanediol salicylate | 2.000 |
| Arachidic alcohol | 1.650 |
| Tromethamine | 1.180 |
| Cetyl alcohol | 1.000 |
| Salicylic acid | 1.000 |
| Ascorbyl glucoside | 1.000 |
| Glycine | 1.000 |
| Tocopheryl acetate | 1.000 |
| Behenyl alcohol | 0.900 |
| Squalane | 0.790 |
| Sodium citrate | 0.660 |
| PPG-12/SMDI Copolymer | 0.500 |
| Arachidyl glucoside | 0.450 |
| Perfume | 0.400 |
| *Sclerotium* gum | 0.160 |
| Cetearyl alcohol | 0.130 |
| Citric acid | 0.110 |
| Sepigel 305* | 0.100 |
| Preservative system | QS |

*A product which is marketed by the Seppic company.

Anti-acneic Cream No 2

| Water | QS 100% |
|---|---|
| Isononyl Isononanoate | 7.000 |
| Di-C$_{12-13}$ malate | 7.000 |
| Isocetyl stearate | 5.000 |
| Butylene glycol | 3.000 |
| *Oryza sativa* | 2.500 |
| Avocado peptide extract | 2.000 |
| C7 Sugars (heptitol) | 1.000 |
| Dicaprylyl ether | 2.000 |
| Silanediol salicylate | 2.000 |
| Arachidic alcohol | 1.650 |
| Tromethamine | 1.180 |
| Cetyl alcohol | 1.000 |
| Salicylic acid | 1.000 |
| Ascorbyl glucoside | 1.000 |
| Glycine | 1.000 |
| Tocopheryl acetate | 1.000 |
| Behenyl alcohol | 0.900 |
| Squalane | 0.790 |
| Sodium citrate | 0.660 |
| PPG-12/SMDI Copolymer | 0.500 |
| Arachidyl glucoside | 0.450 |
| Perfume | 0.400 |
| *Sclerotium* gum | 0.160 |
| Cetearyl alcohol | 0.130 |
| Citric acid | 0.110 |
| Sepigel 305* | 0.100 |
| Preservative system | QS |

*A product which is marketed by the Seppic company.

Foaming Emulsion for Cleaning Atopic Skins

| Water | QS 100 |
|---|---|
| Arlatone duo* | 20.00000 |
| Coco glucoside | 12.00000 |
| Hydroxypropyl Guar | 2.00000 |
| Avocado peptide extract | 2.000 |
| Hydrogenated Glyceryl PEG-200 palmate | 1.10000 |
| Glyceryl PEG-7 Cocoate | 1.10000 |
| Silanediol salicylate | 1.00000 |
| Cocamide DEA | 1.00000 |
| Caprylol Glycine | 0.50000 |
| Potassium sorbate | 0.50000 |
| Polyquaternium 10 | 0.40000 |
| Perfume | 0.40000 |
| Citric acid | 0.30000 |
| Zinc PCA | 0.20000 |

*A product which is marketed by the Quissamo company.

Cleaning & Foaming Emulsion for Personal Hygiene

| Water | QS 100 |
|---|---|
| Arlatone duo* | 20.00000 |
| Coco glucoside | 12.00000 |
| Hydroxypropyl Guar | 2.00000 |
| Avocado peptide extract | 2.000 |
| Avocado sugars | 1.00 |
| Lupine peptides | 2.00 |
| Hydrogenated Glyceryl PEG-200 palmate | 1.10000 |
| Glyceryl PEG-7 Cocoate | 1.10000 |
| Silanediol salicylate | 1.00000 |
| Cocamide DEA | 1.00000 |
| Caprylol Glycine | 0.50000 |
| Potassium sorbate | 0.50000 |
| Polyquaternium 10 | 0.40000 |
| Perfume | 0.40000 |
| Citric acid | 0.30000 |
| Zinc PCA | 0.20000 |

*A product which is marketed by the Quissamo company.

Cleaning Water for Sensitive Skin

| INGREDIENTS | % |
|---|---|
| CAPRYLOYL GLYCINE | 0 à 1% |
| SODIUM BASE LIQUOR | 0 à 1% |
| SEQUESTERING AGENT | 0 à 1% |
| BUTYLENE GLYCOL | 1 à 5% |
| LUPINE PEPTIDES | 0.01 à 5% |
| AVOCADO PEPTIDE EXTRACT | 0.01 à 5% |
| PRESERVATIVES | 0 à 1% |
| PEG-32 | 1 à 5% |
| PEG-7 PALMCOCOATE | 1 à 5% |
| ZINC GLUCONATE | 0 à 1% |
| CITRIC ACID | 0 à 1% |
| PURIFIED WATER | QS 100% |
| PERFUME | 0 à 1% |
| POLOXAMER 184 | 1 à 5% |

Anti-Ageing Emulsion

| INGREDIENTS | % |
|---|---|
| LIQUID ISOPARAFFINE | 5 à 20% |
| ISOLETYL STEARATE | 5 à 20% |
| HYDROXYSTEARATE AL - MG | 5 à 20% |
| ABIL WE 09 | 1 à 5% |
| GLYCEROL | 1 à 5% |
| PETROLATUM | 1 à 5% |
| MICRONISED ZINC OXIDE | 1 à 5% |
| BUTYLENE GLYCOL | 1 à 5% |
| MACA PEPTIDE EXTRACT | 0.01 à 5% |
| AVOCADO PEPTIDE EXTRACT | 0.01 à 5% |
| ISONONYL ISONONANOAT | 1 à 5% |
| BEE'S WAX | 1 à 5% |
| SODIUM TARTRATE | 1 à 5% |

-continued

| INGREDIENTS | % |
| --- | --- |
| SODIUM CHLORIDE | 0 à 5% |
| GLYCINE | 1 à 5% |
| PRESERVATIVES | 0 à 1% |
| CHOLESTEROL | 0 à 1% |
| PHYTOSPHINGOSINE | 0 à 1% |
| TARTRIC ACID | 0 à 1% |
| PURIFIED WATER | QS 100% |

Skin Repair Emulsion

| INGREDIENTS | % |
| --- | --- |
| HYDROGENATED POLYDECENE | 5 à 20% |
| LAURYLGLUCOSIDE-GLYSTEARATE | 1 à 5% |
| DICAPRYLYL CARBONATE | 1 à 5% |
| GLYCEROL | 5 à 20% |
| CARBOPOL | 0 à 1% |
| XANTHAN GUM | 0 à 1% |
| QUINOA PEPTIDE EXTRACT | 0.01 à 5% |
| AVOCADO PEPTIDE EXTRACT | 0.01 à 5% |
| SODIUM BASE LIQUOR | 0 à 1% |
| PRESERVATIVES | 0 à 1% |
| CITRIC ACID | 0 à 1% |
| PURIFIED WATER | QS 100% |

Cream for Dry Skin

| INGREDIENTS | % |
| --- | --- |
| SWEET ALMOND OIL | 1 à 5% |
| CORN OIL | 1 à 5% |
| STEARIC ACID | 1 à 5% |
| CETYL ALCOHOL C16 C18 | 0 à 1% |
| ANTI-FOAMING AGENT 70414 | 0 à 1% |
| LAURY ALCOHOL 11OE | 1 à 5% |
| MONOLAURATE PEG 300 | 0 à 1% |
| GLYCEROL MONOLEATE | 0 à 1% |
| GLYCEROL MONOSTEARATE | 1 à 5% |
| SUNFLOWER SEED OIL UNSAPONIFIABLES | 0.01 à 5% |
| AVOCADO PEPTIDE EXTRACT | 0.01 à 5% |
| PRESERVATIVES | 0 à 1% |
| CITRIC ACID | 0 à 1% |
| TRISODIUM CITRATE | 0 à 1% |
| PURIFIED WATER | QS 100% |
| PERFUME | 0 à 1% |
| PEANUT OIL | 1 à 5% |
| HYDROGENATED PALM OIL | 1 à 5% |

Soothing Spray

| INGREDIENTS | % |
| --- | --- |
| PURIFIED WATER | QS 100% |
| TRILAURETH-4 PHOSPHATE | 1 à 5% |
| DICAPRYLYL CARBONATE | 1 à 5% |
| BUTYLENE GLYCOL | 1 à 5% |
| ERYTHRITYL ESTER | 1 à 5% |
| PETROLATUM OIL | 1 à 5% |
| SHEA BUTTER | 0 à 1% |
| VEGETABLE OIL | 0 à 1% |
| PRESERVATIVES | 0 à 1% |
| OX100 | 0.01 à 5% |
| AVOCADO PEPTIDE EXTRACT | 0.01 à 5% |
| SODIUM BASE LIQUOR | 0 à 1% |
| PERFUME | 0 à 1% |
| XANTHAN GUM | 0 à 1% |
| CARBOPOL | 0 à 1% |
| SEQUESTRING AGENT | 0 à 1% |
| CITRIC ACID | 0 à 1% |

Sunscreen Cream SPF 50+

| INGREDIENTS | % |
| --- | --- |
| PURIFIED WATER B4 | QS 100% |
| TITANIUM OXIDE | 10 à 20% |
| CYCLOPENTASILOXANE | 5 à 15% |
| OCTYL PALMITATE | 5 à 15% |
| C12-C15 ALKYL BENZOATE | 5 à 10% |
| DECYL PENTANOATE | 5 à 10% |
| ZINC OXIDE | 5 à 10% |
| GLYCEROL | 1 à 5% |
| PEG-45/DODECYL GLYCOL COPOLYMER | 1 à 5% |
| AVOCADO PEPTIDE EXTRACT | 0.01 à 5% |
| SODIUM CHLORIDE | 1 à 5% |
| DEXTRIN PALMITATE | 1 à 2% |
| VITAMIN E | 0 à 2% |
| PRESERVATIVES | 0 à 2% |
| HYDROXYPROPYL GUAR | 0 à 1% |
| *ALOE VERA* | 0 à 1% |
| SODIUM BASE LIQUOR | 0 à 1% |
| EDTA 2 Na | 0 à 1% |
| GLUCONATE ZINC | 0 à 1% |

The invention claimed is:

1. A method for the protection of skins selected from the group consisting of:
immature newborn infants' or children's skins;
pathological immature newborn infants' or children's skins;
healthy or pathological skins in adults or aged individuals;
skins which have been weakened by an aggression from environment; or
skins with a deficiency in the skin barrier;
comprising administering a drug comprising 0.1% to 20% by weight of an avocado peptide extract in relation to the total weight of the drug, wherein said avocado peptide extract is obtained by enzymatic hydrolysis, and an appropriate excipient to a patient in need thereof.

2. The method according to claim 1, wherein 50% by weight of peptides in the extract, compared to the total peptides by weight in the extract, are made up of 10-30 amino acids.

3. The method according to claim 1, wherein the drug further comprises D-mannoheptulose and/or perseitol.

4. The method according to claim 1, wherein the source of D-mannoheptulose and/or perseitol is a hydrosoluble avocado sugar extract.

5. The method according to claim 1, to protect the skin from ageing or photoageing.

6. The method according to claim 1, wherein 50% by weight of peptides in the extract, compared to the total peptides weight in the extract, are made up of less than 30 amino acids.

7. The method according to claim 1, wherein at least 50% by weight of peptides in the extract, compared to the total peptides weight in the extract, are made up of 10-30 amino acids.

8. A process for the cosmetic treatment of sensitive, irritated, allergic, dry, aged, intolerant skins and/or mucosae, with a deficiency in the skin barrier, skins and/or mucosae, which have been weakened by an aggression from the environment, skins and/or mucosae with reddenings or with an non pathological immunological imbalance, comprising applying onto the skin and/or the mucosae a composition comprising 0.1% to 20% by weight of an avocado peptide extract in relation to the total weight of the composition, wherein said avocado peptide extract is obtained by enzymatic hydrolysis, and an appropriate excipient, to a patient in need thereof.

9. The process according to claim 8, wherein the composition further comprises D-mannoheptulose and/or perseitol.

10. The process according to claim 8, wherein the source of D-mannoheptulose and/or perseitol is an avocado sugar hydrosoluble extract.

11. A process according to claim 8 for the cosmetic treatment of aged skin and/or mucosae.

12. The method according to claim 8, wherein 50% by weight of peptides in the extract, compared to the total peptides weight in the extract, are made up of less than 30 amino acids.

13. The method according to claim 8, wherein at least 50% by weight of peptides in the extract, compared to the total peptides weight in the extract, are made up of 10-30 amino acids.

* * * * *